US008273536B2

(12) United States Patent
Costa et al.

(10) Patent No.: US 8,273,536 B2
(45) Date of Patent: Sep. 25, 2012

(54) MARKS AS MODIFERS OF THE PTEN PATHWAY AND METHODS OF USE

(75) Inventors: Michael R. Costa, San Francisco, CA (US); Garth Joseph McGrath, San Rafael, CA (US); Kim Lickteig, Highland Park, IL (US); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 98 days.

(21) Appl. No.: 10/556,937

(22) PCT Filed: Jun. 18, 2004

(86) PCT No.: PCT/US2004/019533
§ 371 (c)(1),
(2), (4) Date: Oct. 31, 2006

(87) PCT Pub. No.: WO2005/010148
PCT Pub. Date: Feb. 3, 2005

(65) Prior Publication Data
US 2007/0059698 A1    Mar. 15, 2007

Related U.S. Application Data

(60) Provisional application No. 60/479,768, filed on Jun. 19, 2003.

(51) Int. Cl.
*C12Q 1/68* (2006.01)
*G01N 33/53* (2006.01)
*C07H 21/04* (2006.01)
*C12P 21/06* (2006.01)

(52) U.S. Cl. .............. 435/6.14; 435/226; 435/320.1; 435/325; 536/23.2

(58) Field of Classification Search .................. None
See application file for complete search history.

(56) References Cited

U.S. PATENT DOCUMENTS

2002/0025931 A1* 2/2002 Meyers et al. .......... 514/12
2002/0150954 A1 10/2002 Durden

FOREIGN PATENT DOCUMENTS

WO    WO 96/13592 A2    5/1996
WO    WO 02/098890 A2    12/2002

OTHER PUBLICATIONS

MARK, a Novel Family of Protein Kinases That Phosphorylate a Microtubule Associated protein and Trigger Microtubule Disruption Cell. Drewes et al vol. 89, 297-308, 1997).*
Phosphorylation of MAP2c and MAP4 by MARK kinases leads to the Destabilization of Microtubules in cells. Ebneth et al in Cell Motility and the cytoskeleton. vol. 44:209-224, 1999.*
Martinez et al (Synthetic small inhibiting RNAs: efficient tools to inactivate oncogenic mutations and restore p53 pathways. Proc. Natl Acad. Sci. USA, 99, 14849-14854 (2002.*

Arora, Vikram et al. Phosphorodiamidate Morpholino Antisense Oligomers Inhibit Expression of Human Cytochrome p450 3A4 and Alter Selected Drug Metabolism Drug metabolism and disposition vol. 30, No. 7 p. 757-762.*
Gererd Drewes et al. MARK, a Novel Family of Protein Kinases That Phosphorylate a Microtubule Associated protein and Trigger Microtubule Disruption. Cell vol. 89, 297-308, 1997.*
Summerton et al Morpholino antisense oligomers: the case for an RNase H-independent structural type (Biochimica et Biophysica Acta 1489 (1999) 141-158.*
Stein et al A Specificity Comparison of four antisense types: Morpholino, 2'-OMethyl RNA, DNA, and Phosphorothioate DNA. Antisense & Nucleic acid Drug Development 7:151-157 (1997.*
Martinez et al. Synthetic small inhibiting RNAs: Efficient tools to inactivate oncogenic mutations and restore p53 pathways PNAS vol. 99 No. 23 pp. 14849-14854 Oct. 28, 2002.*
Hong Sun PTEN modulates cell cycle progression and cell survival by regulating phosphatidylinositol 3,4,5,-trisphosphate and Akt/protein kinase B signaling pathway. PNAS May 25, 1999 vol. 96 No. 11 6199-6204.*
Patel et al. Tumor suppressor and anti-inflammatory actions of PPARgamma agonists are mediated via upregulation of PTEN Current Biology (2001), 11:764-768).*
Drewes G. et al. MARK, a Novel Family of Protein Kinases the phosphorylate Microtubule-Assocaited Proteins and Trigger Microtubule Districution. Cell, Apr. 18, 1997, vol. 89, pp. 297-308.
Mills Gordon B. et al.: "Linking molecular diagnostics: Inhibition of the FRAP/RAFT/TOR component of the PI3k pathway preferentially blocks PTEN mutant cells in vitro and in vivo" Proceedings of the National Academy of Sciences of the United States of America; vol. 98, No. 18; Aug. 28, 2001; pp. 10031-10033.
Farrow Buckminster et al.: "Activation of PPARgamma increases PTEN expression in pancreatic cancer cells," Biochemical and Biophysical Research Communications; vol. 301, No. 1; Jan. 31, 2003; pp. 50-53.
Patel Lisa et al.: "Tumor suppressor and anti-inflammatory actions of PPARgamma agonists are mediated via upregulation of PTEN," Current Biology; vol. 11, No. 10; May 15, 2001; pp. 764-768.
Simpson Laura et al.: "PTEN: Life as a tumor suppressor," Experimental Cell Research; vol. 264, No. 1; Mar. 10, 2001; pp. 29-41.
Guo S. et al.: "PAR-1, a gene required for establishing polarity in *C. elegans* embryos, encodes a putative SER/THR kinase that is asymmetrically distributed," Cell, Cell Press, Cambridge, NA, US; vol. 81; May 19, 1995; pp. 611-620.
Drews G. et al.: "MAPs, MARKs and microtubule dynamics," Trends in Biochemical Sciences, Elsevier, Haywards, GB; vol. 23, No. 8; Aug. 1, 1998; pp. 307-311.
Genbank Reference No. 17382968, entitled: "Sequence 25 from Patent WO0174851," dated Nov. 30, 2001.
Genbank Reference No. 27597093, entitled: "*Homo sapiens* SNF1-like kinase (SNF1LK), mRNA," dated Apr. 7, 2003.
Genbank Reference No. 23620491, entitled: "*Homo sapiens* salt-inducible kinase 1, mRNA (cDNA clone MGC:33415 Image:4831049), complete cds," dated Oct. 9, 2002.
Genbank Reference No. 39812204, entitled: "*Homo sapiens* SIK family kinase 3 (SIK3), mRNA," dated Apr. 24, 2003.
Genbank Reference No. 13386467, entitled: "*Homo sapiens* KIAA0999 protein (KIAA0999), mRNA," dated Apr. 24, 2003.

(Continued)

*Primary Examiner* — Kagnew H Gebreyesus
(74) *Attorney, Agent, or Firm* — McDonnell Boehnen Hulbert & Berghoff LLP

(57) ABSTRACT

Human MARK genes are identified as modulators of the PTEN pathway, and thus are therapeutic targets for disorders associated with defective PTEN function. Methods for identifying modulators of PTEN, comprising screening for agents that modulate the activity of MARK are provided.

5 Claims, No Drawings

OTHER PUBLICATIONS

Genbank Reference No. 14133228, entitled: "*Homo sapiens* mRNA for KIAA0999 protein, partial cds," dated May 17, 2001.
Genbank Reference No. 30156409, entitled: "*Homo sapiens* KIAA0781 protein (KIAA0781), mRNA," dated Apr. 28, 2003.
Genbank Reference No. 22064826, entitled: "*Homo sapiens* KIAA0781 protein (KIAA0781), mRNA," dated Apr. 10, 2003.
Genbank Reference No. 30314571, entitled: "*Homo sapiens* LOH11CR1I gene, loss of heterozygosity, 11, chromosomal region 1 gene I product," May 2, 2003.
Genbank Reference No. 38569459, entitled: "*Homo sapiens* salt-inducible kinase 2 (SIK2), mRNA," dated Dec. 1, 2003.
Genbank Reference No. 9978891, entitled: "Probable serine/threonine-protein kinase SNF1LK," dated Oct. 16, 2001.
Genbank Reference No. 27597094, entitled: "SNF1-like kinase [*Homo sapiens*]," dated Apr. 7, 2003.
Genbank Reference No. 14133229, entitled: "KIAA0999 protein [*Homo sapiens*]," dated May 17, 2001.
Genbank Reference No. 14770402, entitled: "similar to hypothetical protein [*Homo sapiens*]," dated Apr. 28, 2003.
Genbank Reference No. 38569460, entitled: "serine/threonine-protein kinase SIK2 [*Homo sapiens*]," dated Dec. 1, 2003.

* cited by examiner

```
                        SEQUENCE LISTING

<160> NUMBER OF SEQ ID NOS: 18

<210> SEQ ID NO 1
<211> LENGTH: 2349
<212> TYPE: DNA
<213> ORGANISM: Homo sapiens

<400> SEQUENCE: 1
atggttatca tgtcggagtt cagcgcggac cccgcgggcc agggtcaggg ccagcagaag      60
cccctccggg tgggtttta  cgacatcgag cggaccctgg gcaaaggcaa cttcgcggtg     120
gtgaagctgg cgcggcatcg agtcaccaaa acgcaggttg caataaaaat aattgataaa     180
acacgattag attcaagcaa tttggagaaa atctatcgtg aggttcagct gatgaagctt     240
ctgaaccatc cacacatcat aaagctttac caggttatgg aaacaaagga catgctttac     300
atcgtcactg aatttgctaa aaatggagaa atgtattatt tgacttccaa cgggcacctg     360
agtgagaacg aggcgcggaa gaagttctgg caaatcctgt cggccgtgga gtactgtcac     420
gaccatcaca tcgtccaccg ggacctcaag accgagaacc tcctgctgga tggcaacatg     480
gacatcaagc tggcagattt tggatttggg aatttctaca gtcaggaga gcctctgtcc     540 acgtggtgtg ggagccccc  gtatgccgcc ccggaagtct ttgaggggaa ggagtatgaa     600
ggcccccagc tggacatctg ggtaggcctg ggcgtggtgc tgtacgtcct ggtctgcggt     660
tctctcccct tcgatgggcc taacctgccg acgctgagac agcgggtgct ggagggccgc     720
ttccgcatcc ccttcttcat gtctcaagac tgtgagagcc tgatccgccg catgctggtg     780
gtggaccccg ccaggcgcat caccatcgcc cagatccggc agcaccggtg gatgcgggct     840 gagcctgct  tgccgggacc cgcctgcccc gccttctccg cacacagcta cacctccaac     900
ctgggcgact acgatgagca ggcgctgggt atcatgcaga ccctgggcgt ggaccggcag     960
```

-continued

| | |
|---|---|
| aggacggtgg agtcactgca aaacagcagc tataaccact tgctgccat ttattacctc | 1020 |
| ctccttgagc ggctcaagga gtatcggaat gcccagtgcg cccgccccgg gcctgccagg | 1080 |
| cagccgcggc ctcggagctc ggacctcagt ggtttggagg tgcctcagga aggtctttcc | 1140 |
| accgacccttt tccgacctgc cttgctgtgc ccgcagccgc agaccttggt gcagtccgtc | 1200 |
| ctccaggccg agatggactg tgagctccag agctcgctgc agcccttgtt cttcccggtg | 1260 |
| gatgccagct gcagcggagt gttccggccc cggcccgtgt ccccaagcag cctgctggac | 1320 |
| acagccatca gtgaggaggc caggcagggg ccgggcctag aggaggagca ggacacgcag | 1380 |
| gagtccctgc ccagcagcac gggccggagg cacaccctgg ccgaggtctc cacccgcctc | 1440 |
| tccccactca ccgcgccatg tatagtcgtc tcccccttcca ccacggcaag tcctgcagag | 1500 |
| ggaaccagct ctgacagttg tctgaccttc tctgcgagca aaagccccgc ggggctcagt | 1560 |
| ggcaccccgg ccactcaggg gctgctgggc gcctgctccc cggtcaggct ggcctcgccc | 1620 |
| ttcctggggt cgcagtccgc caccccagtg ctgcaggctc agggggggctt gggaggagct | 1680 |
| gttctgctcc ctgtcagctt ccaggaggga cggcgggcgt cggacacctc actgactcaa | 1740 |
| gggctgaagg cctttcggca gcagctgagg aagaccacgc ggaccaaagg gtttctggga | 1800 |
| ctgaacaaaa tcaaggggct ggctcgccag gtgtgccagg ccccgccag ccgggccagc | 1860 |
| aggggcggcc tgagccccttt ccacgcccct gcacagagcc caggcctgca cggcggcgca | 1920 |
| gccggcagcc gggagggctg gagcctgctg gaggaggtgc tagagcagca gaggctgctc | 1980 |
| cagttacagc accaccccggc cgctgcaccc ggctgctccc aggccccccca gccggccct | 2040 |
| gccccgtttg tgatcgcccc ctgtgatggc cctggggctg ccccgctccc cagcaccctc | 2100 |
| ctcacgtcgg ggctcccgct gctgccgccc ccactcctgc agaccggcgc gtccccggtg | 2160 |
| gcctcagcgg cgcagctcct ggacacacac ctgcacattg gcaccggccc caccgccctc | 2220 |
| cccgctgtgc ccccaccacg cctggccagg ctggccccag ttgtgagcc cctggggctg | 2280 |
| ctgcaggggg actgtgagat ggaggacctg atgccctgct ccctaggcac gtttgtcctg | 2340 |
| gtgcagtga | 2349 |

<210> SEQ ID NO 2
<211> LENGTH: 2607
<212> TYPE: DNA
<213> ORGANISM: Homo sapiens

<400> SEQUENCE: 2

| | |
|---|---|
| gggactgggg gctccgcggg cacggatgga gccgaccgcg ggcggcgggg gcgctggtgg | 60 |
| gctctgagct ctgtgcggcc ccgcaggtgc gcgcggagcc atggttatca tgtcggagtt | 120 |
| cagcgcggac cccgcgggcc agggtcaggg ccagcagaag cccctccggg tgggtttttta | 180 |
| cgacatcgag cggaccctgg gcaaaggcaa cttcgcggtg gtgaagctgg cgcggcatcg | 240 |
| agtcaccaaa acgcaggtag caataaaaat aattgataaa acacgattag attcaagcaa | 300 |
| tttggagaaa atctatcgtg aggttcagct gatgaagctt ctgaaccatc cacacatcat | 360 |
| aaagctttac caggtagtta tggaaacaaa ggacatgctt tacatcgtca ctgaatttgc | 420 |
| taaaaatgga gaaatgtttg attatttgac ttccaacggg cacctgagtg agaacgaggc | 480 |
| gcggaagaag ttctgcaaa tcctgtcggc cgtggagtac tgtcacgacc atcacatcgt | 540 |
| ccaccgggac ctcaagaccg agaacctcct gctggatggc aacatggaca tcaagctggc | 600 |
| aggcacggaa gatttggat ttgggaattt ctacaagtca ggagagcctc tgtccacgtg | 660 |
| gtgtgggagc ccccgtatg ccgccccgga agtctttgag gggaaggagt atgaaggccc | 720 |

| | |
|---|---|
| ccagctggac atctggagcc tgggcgtggt gctgtacgtc ctggtctgcg gttctctccc | 780 |
| tcccttcgat gggcctaacc tgccgacgct gagacagcgg gtgctggagg ccgcttccg | 840 |
| catcccttc ttcatgtctc aagactgtga gagcctgatc cgccgcatgc tggtggtgga | 900 |
| ccccgccagg cgcatcacca tcgcccagat ccggcagcac cggtggatgc gggctgagcc | 960 |
| ctgcttgccg ggacccgcct gccccgcctt ctccgcacac agctacacct ccaacctggg | 1020 |
| cgactacgat gagcaggcgc tgggtatcat gcagaccctg ggcgtggacc ggcagaggac | 1080 |
| ggtggagtca ctgcaaaaca gcagctataa ccactttgct gccatttatt acctcctcct | 1140 |
| tgagcggctc aaggagtatc ggaatgccca gtgcgcccgc ccgggcctg ccaggcagcc | 1200 |
| gcggcctcgg agctcggacc tcagtggttt ggaggtggtg cctcaggaag gtctttccac | 1260 |
| cgacccttc cgacctgcct tgctgtgccc gcagccgcag accttggtgc agtccgtcct | 1320 |
| ccaggccgag atggactgtg agctccagag ctcgctgcag tggcccttgt tcttcccggt | 1380 |
| ggatgccagc tgcagcggag tgttccggcc ccggcccgtg tccccaagca gcctgctgga | 1440 |
| cacagccatc agtgaggagg ccaggcaggg gccgggccta gaggaggagc aggacacgca | 1500 |
| ggagtccctg cccagcagca cgggccggag gcacaccctg gccgaggtct ccacccgcct | 1560 |
| ctccccactc accgcgccat gtaaggtctc ccctccacc acggcaagtc ctgcagaggg | 1620 |
| aaccagctct gacagttgtc tgaccttctc tgcgagcaaa agcccgcgg ggctcagtgg | 1680 |
| cacccccggcc actcaggggc tgctgggcgc ctgctccccg gtcaggctgg cctcgccctt | 1740 |
| cctggggtcg cagtccgcca ccccagtgct gcaggctcag gggggcttgg gaggagctgt | 1800 |
| tctgctccct gtcagcttcc aggagggacg gcgggcgtcg gacacctcac tgactcaagg | 1860 |
| tgggctgaag gcctttcggc agcagctgag gaagaccacg cggaccaaag gtttctggg | 1920 |
| actgaacaaa atcaaggggc tggctcgcca ggtgtgccag gtccctgcca gccgggccag | 1980 |
| caggggcggc ctgagcccct ccacgcccc tgcacagagc ccaggcctgc acggcggcgc | 2040 |
| agccggcagc cgggagggct ggagcctgct ggaggaggtg ctagagcagc agaggaggct | 2100 |
| gctccagtta cagcaccacc cggccgctgc accggctgc tcccaggccc ccagccggc | 2160 |
| ccctgccccg tttgtgatcg ccccctgtga tggccctggg gctgccccgc tcccagcac | 2220 |
| cctcctcacg tcggggctcc cgctgctgcc gccccactc ctgcagaccg gcgcgtcccc | 2280 |
| ggtggcctca gcgcgcagc tcctggacac acacctgcac attggcaccg gcccaccgc | 2340 |
| cctccccgct gtgcccccac cacgcctggc caggctggcc ccaggttgtg agcccctggg | 2400 |
| gctgctgcag gggactgtg agatggagga cctgatgccc tgctccctag gcacgtttgt | 2460 |
| cctggtgcag tgagggcagc cctgcatcct ggcacggaca ctgactctta cagcaataac | 2520 |
| ttcagaggag gtgaagacat ctggcctcaa agccaagaac tttctagaag cgaaataagc | 2580 |
| aatacgttag gtgttttggc tttttag | 2607 |

<210> SEQ ID NO 3
<211> LENGTH: 2427
<212> TYPE: DNA
<213> ORGANISM: Homo sapiens

<400> SEQUENCE: 3

| | |
|---|---|
| gtgggctctg agctctgtgc ggccccgcag gtgcgcgcgg agccatggtt atcatgtcgg | 60 |
| agttcagcgc ggaccccgcg ggccagagtc agggccagca gaagcccctc cgggtgggtt | 120 |
| tttacgacat cgagcggacc ctgggcaaag gcaacttcgc ggtggtgaag ctggcgcggc | 180 |
| atcgagtcac caaaacgcag gttgcaataa aaataattga taaaacacga ttagattcaa | 240 |

-continued

```
gcaatttgga gaaaatctat cgtgaggttc agctgatgaa gcttctgaac catccacaca    300
tcataaagct ttaccaggtt atggaaacaa aggacatgct ttacatcgtc actgaatttg    360
ctaaaaatgg agaaatgttt gattatttga cttccaacgg gcacctgagt gagaacgagg    420
cgcggaagaa gttctggcaa atcctgtcgg ccgtggagta ctgtcacgac catcacatcg    480
tccaccggga cctcaagacc gagaacctcc tgctggatgg caacatggac atcaagctgg    540
cagattttgg atttgggaat ttctacaagt caggagagcc tctgtccacg tggtgtggga    600
gcccccgta tgccgccccg aagtctttg aggggaagga gtatgaaggc cccagctgg      660
acatctggag cctgggcgtg gtgctgtacg tcctggtctg cggttctctc cccttcgatg    720
ggcctaacct gccgacgctg agacagcggg tgctggaggg ccgcttccgc atccccttct    780
tcatgtctca agactgtgag agcctgatcc gccgcatgct ggtggtggac cccgccaggc    840
gcatcaccat cgcccagatc cggcagcacc ggtggatgcg ggctgagccc tgcttgccgg    900
gacccgcctg ccccgccttc tccgcacaca gctacacctc caacctgggc gactacgatg    960
agcaggcgct gggtatcatg cagaccctgg gcgtggaccg gcagaggacg gtggagtcac   1020
tgcaaaacag cagctataac cactttgctg ccatttatta cctcctcctt gagcggctca   1080
aggagtatcg gaatgcccag tgcgcccgcc ccgggcctgc caggcagccg cggcctcgga   1140
gctcggacct cagtggtttg gaggtgcctc aggaaggtct ttccaccgac cctttccgac   1200
ctgccttgct gtgcccgcag ccgcagacct tggtgcagtc cgtcctccag gccgagatgg   1260
actgtgagct ccagagctcg ctgcagtggc ccttgttctt cccggtggat gccagctgca   1320
gcggagtgtt ccggccccgg cccgtgtccc caagcagcct gctggacaca gccatcagtg   1380
aggaggccag gcaggggccg ggcctagagg aggagcagga cacgcaggag tccctgccca   1440
gcagcacggg ccggaggcac accctggccg aggtctccac ccgcctctcc ccactcaccg   1500
cgccatgtat agtcgtctcc ccctccacca cggcaagtcc tgcagaggga accagctctg   1560
acagttgtct gaccttctct gcgagcaaaa gccccgcggg gctcagtggc accccggcca   1620
ctcaggggct gctgggcgcc tgctccccgg tcaggctggc ctcgcccttc ctggggtcgc   1680
agtccgccac cccagtgctg caggctcagg ggggcttggg aggagctgtt ctgctccctg   1740
tcagcttcca ggagggacgg cgggcgtcgg acacctcact gactcaaggg ctgaaggcct   1800
ttcggcagca gctgaggaag accacgcgga ccaaggggtt tctgggactg aacaaaatca   1860
aggggctggc tcgccaggtg tgccaggtcc ctgccagccg ggccagcagg ggcggcctga   1920
gccccttcca cgcccctgca cagagcccag gcctgcacgg cggcgcagcc ggcagccggg   1980
agggctggag cctgctggag gaggtgctag agcagcagag gctgctccag ttacagcacc   2040
acccggccgc tgcacccggc tgctcccagg cccccagcc ggcccctgcc ccgtttgtga   2100
tcgcccctg tgatggccct ggggctgccc cgctccccag cacctcctc acgtcgggc     2160
tcccgctgct gccgccccca ctcctgcaga ccggcgcgtc cccggtggcc tcagcggcgc   2220
agctcctgga cacacacctg cacattggca ccggcccac cgccctcccc gctgtgcccc    2280
caccacgcct ggccaggctg gccccaggtt gtgagcccct ggggctgctg caggggact    2340
gtgagatgga ggacctgatg ccctgctccc taggcacgtt tgtcctggtg cagtgagggc   2400
agccctgcat cctggcacgg acctgac                                        2427
```

<210> SEQ ID NO 4
<211> LENGTH: 2352
<212> TYPE: DNA
<213> ORGANISM: Homo sapiens

<400> SEQUENCE: 4

```
atggttatca tgtcggagtt cagcgcggac cccgcgggcc agggtcaggg ccagcagaag      60
cccctccggg tgggttttta cgacatcgag cggaccctgg gcaaaggcaa cttcgcggtg     120
gtgaagctgg cgcggcatcg agtcaccaaa acgcaggttg caataaaaat aattgataaa     180
acacgattag attcaagcaa tttggagaaa atctatcgtg aggttcagct gatgaagctt     240
ctgaaccatc acacatcat aaagctttac caggttatgg aaacaaagga catgctttac     300
atcgtcactg aatttgctaa aaatggagaa atgtttgatt atttgacttc caacgggcac     360
ctgagtgaga acgaggcgcg gaagaagttc tggcaaatcc tgtcggccgt ggagtactgt     420
cacgaccatc acatcgtcca ccgggacctc aagaccgaga acctcctgct ggatggcaac     480
atggacatca agctggcaga ttttggattt gggaatttct acaagtcagg agagcctctg     540
tccacgtggt gtgggagccc cccgtatgcc gccccggaag tctttgaggg aaggagtat      600
gaaggccccc agctggacat ctggagcctg gcgtggtgc tgtacgtcct ggtctgcggt      660
tctctcccct tcgatgggcc taacctgccg acgctgagac agcgggtgct ggagggccgc     720
ttccgcatcc ccttcttcat gtctcaagac tgtgagagcc tgatccgccg catgctggtg     780
gtggaccccg ccaggcgcat caccatcgcc cagatccggc agcaccggtg gatgcgggct     840
gagccctgct tgccgggacc cgcctgcccc gccttctccg cacacagcta cacctccaac     900
ctgggcgact acgatgagca ggcgctgggt atcatgcaga ccctgggcgt ggaccggcag     960
aggacggtgg agtcactgca aaacagcagc tataaccact ttgctgccat ttattacctc    1020
ctccttgagc ggctcaagga gtatcggaat gcccagtgcg cccgcccgg gctgccagg      1080
cagccgcggc tcggagctc ggaccctcagt ggtttggagg tgcctcagga aggtctttcc    1140
accgaccctt tccgacctgc cttgctgtgc ccgcagccgc agaccttggt gcagtccgtc    1200
ctccaggccg agatggactg tgagctccag agctcgctgc agtggccctt gttcttcccg    1260
gtggatgcca gctgcagcgg agtgttccgg ccccggcccg tgtccccaag cagcctgctg    1320
gacacagcca tcagtgagga ggccaggcag gggccgggcc tagaggagga gcaggacacg    1380
caggagtccc tgcccagcag cacgggccgg aggcacaccc tggccgaggt ctccaccgc     1440
ctctccccac tcaccgcgcc atgtatagtc gtctcccccct ccaccacggc aagtcctgca    1500
gagggaacca gctctgacag ttgtctgacc ttctctgcga gcaaaagccc cgcggggctc    1560
agtggcaccc cggccactca ggggctgctg ggcgcctgct ccccggtcag gctggcctcg    1620
cccttcctgg ggtcgcagtc cgccacccca gtgctgcagg tcaggggggg cttgggagga    1680
gctgttctgc tccctgtcag cttccaggag ggacggcggg cgtcggacac ctcactgact    1740
caagggctga aggcctttcg gcagcagctg aggaagacca cgcggaccaa agggtttctg    1800
ggactgaaca aaatcaaggg gctggctcgc caggtgtgcc aggccccgc cagccgggcc     1860
agcaggggcg gcctgagccc cttccacgcc cctgcacaga gcccaggcct gcacggcggc    1920
gcagccggca gccgggaggg ctggagcctg ctggaggagg tgctagagca gcagaggctg    1980
ctccagttac agcaccaccc ggccgctgca cccggctgct cccaggcccc ccagccggcc    2040
cctgccccgt ttgtgatcgc cccctgtgat ggccctgggg ctgccccgct ccccagcacc    2100
ctcctcacgt cggggctccc gctgctgccg ccccactcc tgcagaccgg cgcgtccccg    2160
gtggcctcag cggcgcagct cctggacaca cacctgcaca ttggcaccgg ccccaccgcc    2220
ctccccgctg tgcccccacc acgcctggcc aggctggccc caggttgtga gcccctgggg    2280
ctgctgcagg gggactgtga gatggaggac ctgatgccct gctccctagg cacgtttgtc    2340
```
ctggtgcagt ga                                                          2352

<210> SEQ ID NO 5
<211> LENGTH: 4726
<212> TYPE: DNA
<213> ORGANISM: Homo sapiens

<400> SEQUENCE: 5

| | | | | | |
|---|---|---|---|---|---|
| ggcagccgga | gcagtaggca | cccgagcagc | gccagcggcc | gagcgggcgg | cttcctggcc  60 |
| tgggcgctcc | ggtggcggcg | gaggtgcgcg | cggagccatg | gttatcatgt | cggagttcag 120 |
| cgcggacccc | gcgggccagg | gtcagggcca | gcagaagccc | ctccgggtgg | ttttttacga 180 |
| catcgagcgg | accctgggca | aggcaacttt | cgcggtggtg | aagctggcgc | ggcatcgagt 240 |
| caccaaaacg | caggttgcaa | taaaaataat | tgataaaaca | cgattagatt | caagcaattt 300 |
| ggagaaaatc | tatcgtgagg | ttcagctgat | gaagcttctg | aaccatccac | acatcataaa 360 |
| gctttaccag | ttatggaaa  | caaggacat  | gctttacatc | gtcactgaat | ttgctaaaaa 420 |
| tggagaaatg | tttgattatt | tgacttccaa | cgggcacctg | agtgagaacg | aggcgcggaa 480 |
| gaagttctgg | caaatcctgt | cggccgtgga | gtactgtcac | gaccatcaca | tcgtccaccg 540 |
| ggacctcaag | accgagaacc | tcctgctgga | tgcaacatg  | gacatcaagc | tggcagattt 600 |
| tggatttggg | aatttctaca | agtcaggaga | gcctctgtcc | acgtggtgtg | ggagcccccc 660 |
| gtatgccgcc | ccggaagtct | ttgaggggaa | ggagtatgaa | ggccccagc  | tggacatctg 720 |
| gagcctgggc | gtggtgctgt | acgtcctggt | ctgcggttct | ctccccttcg | atggccctaa 780 |
| cctgccgacg | ctgagacagc | gggtgctgga | gggccgcttc | cgcatcccct | tcttcatgtc 840 |
| tcaagactgt | gagagcctga | tccgccgcat | gctggtggtg | accccgcca  | ggcgcatcac 900 |
| catcgcccag | atccggcagc | accggtggat | gcgggctgag | ccctgcttgc | cgggacccgc 960 |
| ctgccccgcc | ttctccgcac | acagctacac | ctccaacctg | ggcgactacg | atgagcaggc 1020 |
| gctgggtatc | atgcagaccc | tgggcgtgga | ccggcagagg | acggtggagt | cactgcaaaa 1080 |
| cagcagctat | aaccactttg | ctgccattta | ttacctcctc | cttgagcggc | tcaaggagta 1140 |
| tcggaatgcc | cagtgcgccc | gccccggggc | tgccaggcag | ccgcggcctc | ggagctcgga 1200 |
| cctcagtggt | ttggaggtgc | ctcaggaagg | tcttccacc  | gaccctttcc | gacctgcctt 1260 |
| gctgtgcccg | cagccgcaga | ccttggtgca | gtccgtcctc | caggccgaga | tggactgtga 1320 |
| gctccagagc | tcgctgcagt | ggccccttgtt | cttcccggtg | gatgccagct | gcagcggagt 1380 |
| gttccggccc | cggccccgtgt | ccccaagcag | cctgctggac | acagccatca | gtgaggaggc 1440 |
| caggcagggg | ccgggcctag | aggaggagca | ggacacgcag | gagtccctgc | ccagcagcac 1500 |
| gggccggagg | cacaccctgg | ccgaggtctc | caccgcctc  | tccccactca | ccgcgccatg 1560 |
| tatagtcgtc | tccccctcca | ccacggcaag | tcctgcagag | ggaaccagct | ctgacagttg 1620 |
| tctgaccttc | tctgcgagca | aaagcccgc  | ggggctcagt | ggcaccccgg | ccactcaggg 1680 |
| gctgctgggc | gcctgctccc | cggtcaggct | ggcctcgccc | ttcctggggt | cgcagtccgc 1740 |
| cacccccagtg | ctgcaggctc | agggggggctt | gggaggagct | gttctgctcc | ctgtcagctt 1800 |
| ccaggaggga | cggcgggcgt | cggacacctc | actgactcaa | gggctgaagg | cctttcggca 1860 |
| gcagctgagg | aagaccacgc | ggaccaaagg | gtttctggga | ctgaacaaaa | tcaagggct  1920 |
| ggctcgccag | gtgtgccagg | tccctgccag | ccgggccagc | aggggcggcc | tgagcccctt 1980 |
| ccacgcccct | gcacagagcc | caggcctgca | cggcggcgca | gccggcagcc | gggagggctg 2040 |
| gagcctgctg | gaggaggtgc | tagagcagca | gaggctgctc | cagttacagc | accacccggc 2100 |

```
cgctgcaccc ggctgctccc aggcccccca gccggcccct gcccgtttg tgatcgcccc   2160 ctgtgatggc cctggggctg ccccgctccc cagcaccctc ctcacgtcgg ggctcccgct   2220
gctgccgccc ccactcctgc agaccggcgc gtcccggtg gcctcagcgg cgcagctcct    2280
ggacacacac ctgcacattg gcaccggccc caccgccctc cccgctgtgc ccccaccacg   2340
cctggccagg ctggccccag gttgtgagcc cctggggctg ctgcagggg actgtgagat    2400 ggaggacctg atgccctgct ccctaggcac gtttgtcctg gtgcagtgag ggcagccctg   2460
catcctggca cggacactga ctcttacagc aataacttca gaggaggtga agacatctgg   2520
cctcaaagcc aagaactttc tagaagcgaa ataagcaata cgttaggtgt tttggctttt   2580
tagtttattt ttgttttatt ttttcttgc actgagtgac ctcaactttg agtagggact    2640
ggaaacttta ggaagaaaga taattgaggg gcgtgtctgg gggcggggc aggaggggag    2700 cggggtggag ggaacacgtg cagtgccgtg gtgtggggat ctcggcccct ctctctgggt   2760
tcgtcgtggt tgagatgatt acctcggacg tctacggaaa cgagcgggcg cattgttgtc   2820
cgcttgtgtg tgtgtgtgtg tgtgtgtgtg tgcgcgtgca ttgattacta tccatttctt   2880
tagtcaacgc tctccacttc ctgatttctg ctttaaggaa aactgtgaac tttctgcttc   2940
atgtatcagt tttaaagcag cccaggcaaa gatcatctac agattctagg aattctctcc   3000
cctgaaatca aaacctggaa gactttttt tcttatttta gttgagaagt ttcataaact    3060
gctcaaggat tagttttcca ggactctgcg gaggaacggc aggaagaacc tcagagaggg   3120
cagaggtgac ttcaaagtgc tgggggactcc gtcctgaggg tcacttggcc ctgagcccct   3180
gcgtgccctt gcggaagccc agaagcttct tcctgctgca cctcccgttt ccgctgctgc   3240
tgacgtttat gcatttcatg atgggtcca acaagaacac ctgacttggg tgaagttgtg   3300
caatattgga ggctgactgt agggctgggc agctgggaga caggctcatg gctcatggct   3360
catggctcag ggcggtgcct gccatgggcc gggacccccc tccccacccc ccacctaggc   3420
tttttgggtt ttgttcaagg aaggtaaagt gagaggttta ggtcagtgtt tttaagtttt   3480
tgtttttttt ttaaagcaaa tcctgtatat gtatctacat gggagacagg tagacactac   3540
ttatttgtta cattttgtac tacacgtttg tgttccaggt ttcagcttcc ctcgctcctg    3600
ttgttaagaa gcgtccctgt cagcacaggt gtgcattgag aaggggccc cagggccttc    3660 gctccctcag cactggggtg gaggcggcag gaaggggcgg cccttacctg gcaggtctgg   3720
gcgcaccttt agcaggtgga ctccgtgggg ctccaccagc cagaagcctt tggaaggcaa   3780
cgaaggcaat gctgctccct gagtccagtc cccgccccca aacccagccc aggtgccttc   3840
agctacttcg gcttcttaaa ccctgcagtg ttaaacagag gcattgagaa agggaaagg    3900 cgggtatttt taaaagccaa agattgaccc agttacttga gggtagggag gcgggcccag   3960
tgcaggaggc tgcatccctg gcctgctggt gcccaccggg ggctgtgcct gtgccgggcc   4020
gcagggaagc tggctgcccc cattcctgct gctgctgctg ctgctgctct gtggctgttt   4080
caaagactgg gcgaaaggct gtccggaggg cagaccaggt gccttgccgc agagaaaaca   4140
ccaaagtctc ctgttcgctc ataaagaagt tttggggatg ggagagaatc cagaccatct   4200
tggggcagcc aggcccttgc cttcattttt acagaggtag cacaattgat tccaacacaa   4260
aacttcccct ttttaaaatg atttctgttc taatgccata gatcaaaggc ctcagaaacc   4320
attgtgtgtt tcctctttga agcaatgaca agcactttac tttcacggtg gttttttgttt   4380 tttcttattg ctgtggaacc tcttttggag gacgttaaag gcgtgtttta cttgtttttt   4440
taagagtgtg tgatgtgtgt tttgtagatt tcttgacagt gctgtaatac agacggcaat   4500
```

```
gcaatagcct atttaaagac actacgtgat ctgattgaga tgtacatagt tttttttttt    4560
accataactg aattatttta tctcttatgt taacatgaga aatgtatgcc aaatgattag    4620
ttgatgtatg ttttttaatt taatatttaa ataaaatatt tgggagtata aaaaaaaaaa    4680
aaaaaaaaaa aaaaaaaaaa aaaaaaaaaa aaaaaaaaaa aaaaaa                   4726

<210> SEQ ID NO 6
<211> LENGTH: 4762
<212> TYPE: DNA
<213> ORGANISM: Homo sapiens

<400> SEQUENCE: 6
atgcggcgcg gccccggagg cagcagcagc ggcggcggca gccggagcag taggcacccg      60
agcagcgcca gcggccgagc gggcggcttc ctggcctggg cgctccggtg cggcggagg     120 tgcgcgcgga gccatggtta tcatgtcgga gttcagcgcg accccgcgg gccagggtca     180 gggccagcag aagcccctcc gggtgggttt ttacgacatc gagcggaccc tgggcaaagg    240
caacttcgcg gtggtgaagc tggcgcggca tcgagtcacc aaaacgcagg ttgcaataaa    300
aataattgat aaaacacgat tagattcaag caatttggag aaaatctatc gtgaggttca    360
gctgatgaag cttctgaacc atccacacat cataaagctt taccaggtta tggaaacaaa    420
ggacatgctt tacatcgtca ctgaatttgc taaaaatgga gaaatgtttg attatttgac    480
ttccaacggg cacctgagtg agaacgaggc gcggaagaag ttctggcaaa tcctgtcggc    540
cgtggagtac tgtcacgacc atcacatcgt ccacgggac tcaagaccg agaacctcct     600 gctggatggc aacatggaca tcaagctggc agattttgga tttgggaatt tctacaagtc    660
aggagagcct ctgtccacgt ggtgtgggag cccccgtat gccgcccgg aagtctttga     720 ggggaaggag tatgaaggcc cccagctgga catctggagc ctgggcgtgg tgctgtacgt    780
cctggtctgc ggttctctcc ccttcgatgg gcctaacctg ccgacgctga cagcgggt     840 gctggaggc cgcttccgca tccccttctt catgtctcaa gactgtgaga gcctgatccg    900
ccgcatgctg gtggtggacc ccgccaggcg catcaccatc gcccagatcc ggcagcaccg    960
gtggatgcgg gctgagccct gcttgccggg acccgcctgc cccgccttct ccgcacacag   1020
ctacacctcc aacctgggcg actacgatga gcaggcgctg ggtatcatgc agaccctggg   1080
cgtggaccgg cagaggacgg tggagtcact gcaaaacagc agctataacc actttgctgc   1140
catttattac ctcctccttg agcggctcaa ggagtatcgg aatgcccagt gcgcccgccc   1200
cgggcctgcc aggcagccgc ggcctcggag ctcggacctc agtggttttgg aggtgcctca   1260 ggaaggtctt tccaccgacc ctttccgacc tgccttgctg tgcccgcagc cgcagacctt   1320
ggtgcagtcc gtcctccagg ccgagatgga ctgtgagctc cagagctcgc tgcagtggcc   1380
cttgttcttc ccggtggatg ccagctgcag cggagtgttc cggccccggc ccgtgtcccc   1440
aagcagcctg ctggacacag ccatcagtga ggaggccagg caggggccgg gcctagagga   1500
ggagcaggac acgcaggagt ccctgcccag cagcacgggc cggaggcaca ccctggccga   1560
ggtctccacc cgcctctccc cactcaccgc gccatgtata gtcgtctccc cctccaccac   1620
ggcaagtcct gcagagggaa ccagctctga cagttgtctg accttctctg cgagcaaaag   1680
ccccgcgggg ctcagtggca ccccggccac tcaggggctg ctgggcgcct gctcccggt    1740 caggctggcc tcgcccttcc tggggtcgca gtccgccacc ccagtgctgc aggctcaggg   1800
gggcttggga ggagctgttc tgctccctgt cagcttccag gagggacggc gggcgtcgga   1860
cacctcactg actcaagggc tgaaggcctt tcggcagcag ctgaggaaga ccacgcggac   1920
```

```
caaagggttt ctgggactga acaaaatcaa ggggctggct cgccaggtgt gccaggtccc    1980
tgccagccgg gccagcaggg gcggcctgag cccctccac gccctgcac agagcccagg      2040 cctgcacggc ggcgcagccg gcagccggga gggctggagc ctgctggagg aggtgctaga    2100
gcagcagagg ctgctccagt tacagcacca cccggccgct gcacccggct gctcccaggc    2160
cccccagccg gccctgccc cgtttgtgat cgcccctgt gatggccctg ggctgcccc      2220 gctcccagc accctcctca cgtcggggct cccgctgctg ccgccccac tcctgcagac      2280 cggcgcgtcc ccggtggcct cagcggcgca gctcctggac acacacctgc acattggcac    2340
cggccccacc gccctccccg ctgtgccccc accacgcctg gccaggctgg ccccaggttg    2400
tgagcccctg gggctgctgc aggggactg tgagatggag gacctgatgc cctgctccct    2460
aggcacgttt gtcctggtgc agtgagggca gccctgcatc ctggcacgga cactgactct    2520
tacagcaata acttcagagg aggtgaagac atctggcctc aaagccaaga actttctaga    2580
agcgaaataa gcaatacgtt aggtgttttg gcttttagt ttatttttgt tttatttttt    2640
tcttgcactg agtgacctca actttgagta gggactggaa actttaggaa gaaagataat    2700
tgaggggcgt gtctggggc gggggcagga ggggagcggg gtggagggaa cacgtgcagt     2760
gccgtggtgt gggatctcg gccctctct ctgggttcgt cgtggttgag atgattacct      2820
cggacgtcta cggaaacgag cgggcgcatt gttgtccgct tgtgtgtgtg tgtgtgtgtg    2880
tgtgtgtgcg cgtgcattga ttactatcca tttctttagt caacgctctc cacttcctga    2940
tttctgcttt aaggaaaact gtgaacttc tgcttcatgt atcagtttta aagcagccca     3000
ggcaaagatc atctacagat tctaggaatt ctctccctg aaatcaaaac ctggaagact     3060 ttttttctt atttagttg agaagtttca taaactgctc aaggattagt tttccaggac      3120
tctgcggagg aacggcagga agaacctcag agagggcaga ggtgacttca aagtgctggg    3180
gactccgtcc tgagggtcac ttggccctga gccctgcgt gccttgcgg aagcccagaa     3240 gcttcttcct gctgcacctc ccgtttccgc tgctgctgac gtttatgcat ttcatgatgg    3300
ggtccaacaa gaacacctga cttgggtgaa gttgtgcaat attggaggct gactgtaggg    3360
ctgggcagct gggagacagg ctcatggctc atggctcatg gctcagggcg gtgcctgcca    3420
tgggccggga ccccctccc cacccccac ctaggctttt tgggttttgt tcaaggaagg     3480
taaagtgaga ggtttaggtc agtgttttta agttttgtt ttttttttaa agcaaatcct     3540
gtatatgtat ctacatggga gacaggtaga cactacttat tgttacatt ttgtactaca    3600 cgtttgtgtt ccaggtttca gcttccctcg ctcctgttgt taagaagcgt ccctgtcagc    3660
acaggtgtgc attgaggaag gggcccagg gccttcgctc cctcagcact ggggtggagg    3720
cggcaggaag gggcggccct tacctggcag gtctgggcgc acctttagca ggtggactcc    3780
gtggggctcc accagccaga agcctttgga aggcaacgaa ggcaatgctg ctccctgagt    3840
ccagtccccg cccccaaacc cagcccaggt gccttcagct acttcggctt cttaaaccct    3900
gcagtgttaa acagaggcat tgagaaaggg gaaaggcggg tatttttaaa agccaaagat    3960
tgacccagtt acttgagggt agggaggcgg gcccagtgca ggaggctgca tccctggcct    4020
gctggtgccc accggggct gtgcctgtgc cgggccgcag ggaagctggc tgccccatt     4080 cctgctgctg ctgctgctgc tgctctgtgg ctgtttcaaa gactgggcga aaggctgtcc    4140
ggagggcaga ccaggtgcct tgccgcagag aaaacaccaa agtctcctgt tcgctcataa    4200
agaagttttt gggatgggag agaatccaga ccatcttggg gcagccaggc ccttgccttc    4260 attttacag aggtagcaca attgattcca acacaaaact tccccttttt aaaatgattt     4320
```

```
ctgttctaat gccatagatc aaaggcctca gaaaccattg tgtgtttcct ctttgaagca    4380
atgacaagca ctttactttc acggtggttt ttgttttttc ttattgctgt ggaacctctt    4440
ttggaggacg ttaaaggcgt gttttacttg ttttttttaag agtgtgtgat gtgtgttttg    4500
tagatttctt gacagtgctg taatacagac ggcaatgcaa tagcctattt aaagacacta    4560
cgtgatctga ttgagatgta catagttttt tttttttacca taactgaatt attttatctc    4620
ttatgttaac atgagaaatg tatgccaaat gattagttga tgtatgtttt ttaatttaat    4680
atttaaataa aatatttggg agtataaaaa aaaaaaaaaa aaaaaaaaaa aaaaaaaaa    4740
aaaaaaaaaa aaaaaaaaaa aa                                             4762

<210> SEQ ID NO 7
<211> LENGTH: 6072
<212> TYPE: DNA
<213> ORGANISM: Homo sapiens

<400> SEQUENCE: 7
cagccgcgtc ccccagcccc ggcctcccgc ggacccatgc ccgcccgtat cggctactac      60
gagatcgacc gcaccatcgg caagggcaac ttcgcggtgg tcaagcgggc cacgcacctc     120
gtcaccaagg ccaaggttgc tatcaagatc atagataaga cccagctgga tgaagaaaac     180
ttgaagaaga ttttccggga agttcaaatt atgaagatgc tttgccaccc ccatatcatc     240
aggctctacc aggttatgga gacagaacgg atgatttatc tggtgacaga atatgctagt     300
ggagggaaa tatttgacca cctggtggcc catggtagaa tggcagaaaa ggaggcacgt     360
cggaagttca acagatcgt cacagctgtc tattttttgtc actgtcggaa cattgttcat     420
cgtgatttaa aagctgaaaa tttacttctg gatgccaatc tgaatatcaa aatagcagat     480
tttggtttca gtaacctctt cactcctggg cagctgctga agacctggtg tggcagccct     540
ccctatgctg cacctgaact ctttgaagga aaagaatatg atgggcccaa agtggacatc     600
tggagccttg gagttgtcct ctacgtgctt gtgtgcggtg ccctgccatt tgatggaagc     660
acactgcaga atctgcgggc ccgcgtgctg agtggaaagt tccgcatccc attttttatg     720
tccacagaat gtgagcattt gatccgccat atgttggtgt tagatcccaa taagcgcctc     780
tccatggagc agatctgcaa gcacaagtgg atgaagctag ggacgccga tcccaacttt     840
gacaggttaa tagctgaatg ccaacaacta aggaagaaa gacaggtgga ccccctgaat    900
gaggatgtcc tcttggccat ggaggacatg ggactggaca agaacagac actgcagtca    960
ttaagatcag atgcctatga tcactatagt gcaatctaca gcctgctgtg tgatcgacat   1020
aagagacata aaaccctgcg tctcggagca cttcctagca tgccccgagc cctggccttt   1080
caagcaccag tcaatatcca ggcggagcag gcaggtactg ctatgaacat cagcgttccc   1140
caggtgcagc tgatcaaccc agagaaccaa attgtggagc cggatgggac actgaatttg   1200
gacagtgatg agggtgaaga gccttcccct gaagcattgg tgcgctattt gtcaatgagg   1260
aggcacacag tgggtgtggc tgacccacgc acggaagtta tggaagatct gcagaagctc   1320
ctacctggct ttcctggagt caaccccag gctccattcc tgcaggtggc cctaatgtg     1380
aacttcatgc acaacctgtt gcctatgcaa aacttgcaac caaccgggca acttgagtac   1440
aaggagcagt ctctcctaca gccgcccacg ctacagctgt tgaatggaat gggcccctt    1500
ggccggaggg catcagatgg aggagccaac atccaactgc atgcccagca gctgctgaag   1560
cgcccacggg gaccctctcc gcttgtcacc atgacaccag cagtgccagc agttaccct    1620
gtggacgagg agagctcaga cggggagcca gaccaggaag ctgtgcagag ctctacctac   1680
```

```
aaggactcca acactctgca cctccctacg gagcgtttct cccctgtgcg ccggttctca   1740 gatgggctg cgagcatcca ggccttcaaa gctcacctgg aaaaaatggg caacaacagc   1800
agcatcaaac agctgcagca ggagtgtgag cagctgcaga agatgtacgg ggggcagatt   1860
gatgaaagaa ccctggagaa gacccagcag cagcatatgt ataccagca ggagcagcac   1920 catcaaattc tccagcaaca aattcaagac tctatctgtc ctcctcagcc atctccacct   1980
cttcaggctg catgtgaaaa tcagccagcc ctccttaccc atcagctcca gaggttaagg   2040
attcagcctt caagcccacc ccccaaccac cccaacaacc atctcttcag gcagcccagt   2100
aatagtcctc cccccatgag cagtgccatg atccagcctc acggggctgc atcttcttcc   2160
cagtttcaag cttaccttc ccgcagtgca atctttcagc agcaacctga gaactgttcc   2220
tctcctccca acgtggcact aacctgcttg ggtatgcagc agcctgctca gtcacagcag   2280
gtcaccatcc aagtccaaga gcctgttgac atgctcagca acatgccagg cacagctgca   2340
ggctccagtg ggcgcggcat ctccatcagc cccagtgctg gtcagatgca gatgcagcac   2400
cgtaccaacc tgatggccac cctcagctat gggcaccgtc ccttgtccaa gcagctgagt   2460
gctgacagtg cagaggctca cagcttgaac gtgaatcggt tctcccctgc taactacgac   2520
caggcgcatt tacaccccca tctgtttttcg gaccagtccc ggggttcccc cagcagctac   2580
agcccttcaa caggagtggg gttctctcca acccaagccc tgaaagtccc tccacttgac   2640
caattcccca ccttccctcc cagtgcacat cagcagccgc cacactatac cacgtcggca   2700
ctacagcagg ccctgctgtc tcccacgccg ccagactata caagacacca gcaggtaccc   2760
cacatccttc aaggactgct ttctccccgg cattcgctca ccggccactc ggacatccgg   2820
ctgcccccaa cagagtttgc acagctcatt aaaaggcagc agcaacaacg gcagcagcag   2880
cagcaacagc agcaacagca agaataccag gaactgttca ggcacatgaa ccaaggggat   2940
gcggggagtc tggctcccag ccttggggga cagagcatga cagagcgcca ggctttatct   3000
tatcaaaatg ctgactctta tcaccatcac accagccccc agcatctgct acaaatcagg   3060
gcacaagaat gtgtctcaca ggcttcctca cccacccgc cccacgggta tgctcaccag   3120
ccggcactga tgcattcaga gagcatggag gaggactgct cgtgtgaggg ggccaaggat   3180
ggcttccaag acagtaagag ttcaagtaca ttgaccaaag gttgccatga cagccctctg   3240
ctcttgagta ccggtggacc tggggaccct gaatctttgc taggaactgt gagtcatgcc   3300
caagaattgg ggatacatcc ctatggtcat cagccaactg ctgcattcag taaaaataag   3360
gtgcccagca gagagcctgt catagggaac tgcatggata aagttctcc aggacaagca   3420 gtggagctgc cggatcacaa tgggctcggg tacccagcac gcccctccgt ccatgagcac   3480
cacaggcccc gggccctcca gagacaccac acgatccaga acagcgacga tgcttatgta   3540
cagctggata acttgccagg aatgagtctc gtggctggga aagcacttag ctctgcccgg   3600
atgtcggatg cagttctcag tcagtcttcg ctcatgggca gccagcagtt tcaggatggg   3660
gaaaatgagg aatgtggggc aagcctggga ggtcatgagc acccagacct gagtgatggc   3720
agccagcatt taaactcctc ttgctatcca tctacgtgta ttacagacat tctgctcagc   3780
tacaagcacc ccgaagtctc cttcagcatg gagcaggcag gcgtgtaaca agaaacagag   3840
agttttgtgt acagcttggg aatgaaaagg ttgattgtaa acccacagta tctagcagcg   3900
ttgtgccaaa ttgcccttgt gtttctctcc acccaaaata tcacagctgc tttcctcaca   3960
tttggttcat ccgtgtgctg ttctttggg ttctgagagg gttttgccat gtttgcttgt   4020
atgaccaagt caccaaggaa ataaacagga aggaaatcca tgttctccat cttttgtgaa   4080
```

```
agtatatttg agttggtggt tttttgtttt gtttgggggt ttgtgttttg ttttgttttt    4140
ggtatgtttt cttccagagg tgatatactt tcttttttttt cttcctttct ttttttttctt   4200
tcgttccttt tttgaaacag gagagcaaag cagttagagt tcagaggcca gcggcctcag    4260
ggccactccc tccctagcct tcatcagcag agcaccctcc atcccctgc attgctcttc    4320
tgtgaaagca aatactaaag gatgccatcc tctggaatcc taatggcagg caaagggaga   4380
gaggaagggt gacggcttct ggcacttaga aaacaaaaag aacaaaaaaa gagaaacccc    4440
caagcctgga acgcagagag gtctttactg ctgggatcca cggaaaacat gtctgtccta    4500
gccaagatca tatgaagagt ttggcacgga ggctgagaat gacctggcat agatggtttg    4560
ccagttagga tgtctcaatt tgagcctttg cttttggtgg ataactcagc tcccctcttg    4620
taacctggaa agttggttgc ctttatcatc ctgctggttt tatccatgga ctgaacaccc    4680
aacagcagtg cactatgctt tctatggcat cttttcattct cattttatat tgtgctataa   4740
aaaggattgt ttctccatat atatattata tatgtgtgta tatatataat ataatatatg   4800
tgtatatata tattatatat ataatatata atataatata ttatatatat attatatata   4860
taatatatat ataaaatata tatatatatg ctctcctctt tcagcctctt tgtcacaggg   4920
aagaagtgta ggaggttgcc ttgggccctg cctctctcct aacctcctct tccccactgg   4980
gtaccctcag cccctatatt ttaattcttg atcatgtaga aattgttttt ggtaaatgtt   5040
gatattattg ttattatcat tattaataaa taaagagaaa aggaattttt gtttaaatga   5100
gaaatgttta accagattct gttctatttg aattgtgact tgcacctttt gttcaaagta   5160
tttcctttag gcattgtaat tgtgaacagc tcttacttgt gccagtgaca gatgcagtgg   5220
tctcctttcc ccagttgaag cagtgcatac gcagtagcta ttatttgtgt tatctttatt   5280
tctcttcatt gttagaaacc aaagtcttct ctgctggctg gggctgagag agggtctggg   5340
ttatctcctt ctgatcttca aaacaagaga gagaccttga atacactgac tcttccaccc   5400
ttttttttttc tgggaaagga gagcaagagg tcccgagtcc cctcctagtc tttcatcctg   5460
aatttgcaca gaggaaagcg ggtgcccggc atggccatcc tgatgttgct ggcgggatcc   5520
ccatgcacct tgtccttctc cactgatact ggcagctcgg ctcctggacc caagatccct   5580
tgagtggaat tctgcagtgc aagagccctt cgtgggagct gtcccatgtt tccatggtcc   5640
ccagtctccc ctccacttgg tggggtcacc aactactcac cagaagggg cttaccaaga    5700
aagccctaaa aagctgttga cttatctgcg cttgttccaa ctcttatgcc cccaacctgc    5760
cctaccacca ccacgcgctc agcctgatgt gtttacatgg tactgtatgt atgggagagc   5820
agactgcacc ctccagcaac aacagatgaa agccagtgag cctactaacc gtgccatctt   5880
gcaaactaca ctttaaaaaa aactcattgc tttgtattgt agtaaccaat atgtgcagta   5940
tacgttgaat gtatatgaac atactttcct atttctgttc tttgaaaatg tcagaaatat   6000
tttttctttt ctcattttat gttgaactaa aaaggattaa aaaaaaaatc tccagactca   6060
agttgctaaa aa                                                        6072

<210> SEQ ID NO 8
<211> LENGTH: 1752
<212> TYPE: DNA
<213> ORGANISM: Homo sapiens

<400> SEQUENCE: 8
gacatgctca gcaacatgcc aggcacagct gcaggctcca gtgggcgcgg catctccatc     60
agccccagtg ctggtcagat gcagatgcag caccgtacca acctgatggc caccctcagc    120
```

| | |
|---|---:|
| tatgggcacc gtcccttgtc caagcagctg agtgctgaca gtgcagaggc tcacagcttg | 180 |
| aacgtgaatc ggttctcccc tgctaactac gaccaggcgc atttacaccc ccatctgttt | 240 |
| tcggaccagt cccggggttc ccccagcagc tacagccctt caacaggagt ggggttctct | 300 |
| ccaacccaag ccctgaaagt ccctccactt gaccaattcc ccaccttccc tcccagtgca | 360 |
| catcagcagc cgccacacta taccacgtcg gcactacagc aggccctgct gtctcccacg | 420 |
| ccgccagact atacaagaca ccagcaggta ccccacatcc ttcaaggact gctttctccc | 480 |
| cggcattcgc tcaccggcca ctcggacatc cggctgcccc aacagagtt tgcacagctc | 540 |
| attaaaaggc agcagcaaca acggcagcag cagcagcaac agcagcaaca gcaagaatac | 600 |
| caggaactgt tcaggcacat gaaccaaggg gatgcgggga gtctggctcc cagccttggg | 660 |
| ggacagagca tgacagagcg ccaggctttta tcttatcaaa atgctgactc ttatcaccat | 720 |
| cacaccagcc cccagcatct gctacaaatc agggcacaag aatgtgtctc acaggcttcc | 780 |
| tcacccaccc cgccccacgg gtatgctcac cagccggcac tgatgcattc agagagcatg | 840 |
| gaggaggact gctcgtgtga gggggccaag gatggcttcc aagacagtaa gagttcaagt | 900 |
| acattgacca aaggttgcca tgacagccct ctgctcttga gtaccggtgg acctggggac | 960 |
| cctgaatctt tgctaggaac tgtgagtcat gcccaagaat tggggataca tccctatggt | 1020 |
| catcagccaa ctgctgcatt cagtaaaaat aaggtgccca gcagagagcc tgtcataggg | 1080 |
| aactgcatgg atagaagttc tccaggacaa gcagtggagc tgccggatca caatgggctc | 1140 |
| gggtacccag cacgcccctc cgtccatgag caccacaggc cccgggccct ccagagacac | 1200 |
| cacacgatcc agaacagcga cgatgcttat gtacagctgg ataacttgcc aggaatgagt | 1260 |
| ctcgtggctg ggaaagcact tagctctgcc cggatgtcgg atgcagttct cagtcagtct | 1320 |
| tcgctcatgg gcagccagca gtttcaggat ggggaaaatg aggaatgtgg ggcaagcctg | 1380 |
| ggaggtcatg agcacccaga cctgagtgat ggcagccagc atttaaactc ctcttgctat | 1440 |
| ccatctacgt gtattacaga cattctgctc agctacaagc accccgaagt ctccttcagc | 1500 |
| atggagcagg caggcgtgta acaagaaaca gagagttttg tgtacagctt gggaatgaaa | 1560 |
| aggttgattg taaacccaca gtatctagca gcgttgtgcc aaaattgccct tgtgtttctc | 1620 |
| tccacccaaa atatcacagc tgctttcctc acatttggtt catccgtgtg ctgttctttt | 1680 |
| gggttctgag agggttttgc catgtttgct tgtatgacca agtcaccaag gaaataaaca | 1740 |
| ggaaggaaat cc | 1752 |

<210> SEQ ID NO 9
<211> LENGTH: 4460
<212> TYPE: DNA
<213> ORGANISM: Homo sapiens

<400> SEQUENCE: 9

| | |
|---|---:|
| ggcacgcccg gaggcggggc cgggtgcgtc ctggcggggg gattggcgga gccggagagt | 60 |
| ggcagcgggc atgggcgggg gctgtctcca gggaaacgcg acgctctccg taggcgcagg | 120 |
| gctggcaagc agtcgggacg ggagcgcggg cgtccgcggt ggctgcagtc ccgtcggtct | 180 |
| ccctgctgtc cggcgcgagc tcttcgagtc ttgcttggtg cggtctcgcg acaggagcgc | 240 |
| tgggagccgg ggctagggggg atcccggagc tccgtgggcc ggcgggtgcg ggcggggctg | 300 |
| ccggggccgg gactggggga gccgggcccg cgggccgcct gctgcctccg cccgcgccgg | 360 |
| ggtccccagc cgcccccgct gccgtgtccc ctgcggccgg ccagccgcgt ccccagccc | 420 |
| cggcctcccg cggacccatg cccgcccgta tcggctacta cgagatcgac cgcaccatcg | 480 |

```
gcaagggcaa cttcgcggtg gtcaagcggg ccacgcacct cgtcaccaag gccaaggttg      540
ctatcaagat catagataag acccagctgg atgaagaaaa cttgaagaag attttccggg      600
aagttcaaat tatgaagatg ctttgccacc cccatatcat caggctctac caggttatgg      660
agacagaacg gatgatttat ctggtgacag aatatgctag tggagggaa atatttgacc       720 acctggtggc ccatggtaga atggcagaaa aggaggcacg tcggaagttc aaacagatcg      780
tcacagctgt ctatttttgt cactgtcgga acattgttca tcgtgattta aaagctgaaa      840
atttacttct ggatgccaat ctgaatatca aaatagcaga ttttggtttc agtaacctct      900
tcactcctgg gcagctgctg aagacctggt gtggcagccc tccctatgct gcacctgaac      960
tctttgaagg aaaagaatat gatgggccca agtggacat  ctggagcctt ggagttgtcc     1020
tctacgtgct tgtgtgcggt gccctgccat tgatggaag  cacactgcag aatctgcggg     1080
cccgcgtgct gagtggaaag ttccgcatcc catttttat  gtccacagaa tgtgagcatt     1140
tgatccgcca tatgttggtg ttagatccca ataagcgcct ctccatggag cagatctgca     1200
agcacaagtg gatgaagcta ggggacgccg atcccaactt tgacaggtta atagctgaat     1260
gccaacaact aaaggaagaa agacaggtgg accccctgaa tgaggatgtc ctcttggcca     1320
tggaggacat gggactggac aaagaacaga cactgcagtc attaagatca gatgcctatg     1380
atcactatag tgcaatctac agcctgctgt gtgatcgaca taagagacat aaaaccctgc     1440
gtctcggagc acttcctagc atgccccgag ccctggcctt tcaagcacca gtcaatatcc     1500
aggcggagca ggcaggtact gctatgaaca tcagcgttcc ccaggtgcag ctgatcaacc     1560
cagagaacca aattgtggag ccggatggga cactgaattt ggacagtgat gagggtgaag     1620
agccttcccc tgaagcattg gtgcgctatt tgtcaatgag gaggcacaca gtgggtgtgg     1680
ctgacccacg cacggaagtt atggaagatc tgcagaagct cctacctggc tttcctggag     1740
tcaaccccca ggctccattc ctgcaggtgg cccctaatgt gaacttcatg cacaacctgt     1800
tgcctatgca aaacttgcaa ccaaccgggc aacttgagta caaggagcag tctctcctac     1860
agccgcccac gctacagctg ttgaatggaa tgggcccccct tggccggagg gcatcagatg     1920
gaggagccca catccaactg catgcccagc agctgctgaa gcgcccacgg ggaccctctc     1980
cgcttgtcac catgacacca gcagtgccag cagttacccc tgtggacgag gagagctcag     2040
acggggagcc agaccaggaa gctgtgcaga gctctaccta caaggactcc aacactctgc     2100
acctccctac ggagcgtttc tcccctgtgc gccggttctc agatggggct gcgagcatcc     2160
aggccttcaa agctccaccctg gaaaaaatgg gcaacaacag cagcatcaaa cagctgcagc     2220
aggagtgtga gcagctgcag aagatgtacg gggggcagat tgatgaaaga accctggaga     2280
agacccagca gcagcatatg ttataccagc aggagcagca ccatcaaatt ctccagcaac     2340
aaattcaaga ctctatctgt cctcctcagc catctccacc tcttcaggct gcatgtgaaa     2400
atcagccagc cctccttacc catcagctcc agaggttaag gattcagcct tcaagcccac     2460
ccccaaccca cccaacaac  catctcttca ggcagcccag taatagtcct ccccccatga     2520
gcagtgccat gatccagcct cacggggctg catcttcttc ccagtttcaa ggcttacctt     2580
cccgcagtgc aatctttcag cagcaacctg agaactgttc ctctcctccc aacgtggcac     2640
taacctgctt gggtatgcag cagcctgctc agtcacagca ggtcaccatc caagtccaag     2700
agcctgttga catgctcagc aacatgccag gcacagctgc aggctccagt gggcgcggca     2760
tctccatcag ccccagtgct ggtcagatgc agatgcagca ccgtaccaac ctgatggcca     2820
ccctcagcta tgggcaccgt cccttgtcca agcagctgag tgctgacagt gcagaggctc     2880
```

-continued

| | |
|---|---|
| acagcttgaa cgtgaatcgg ttctcccctg ctaactacga ccaggcgcat ttacaccccc | 2940 |
| atctgttttc ggaccagtcc cggggttccc ccagcagcta cagcccttca acaggagtgg | 3000 |
| ggttctctcc aacccaagcc ctgaaagtcc ctccacttga ccaattcccc accttccctc | 3060 |
| ccagtgcaca tcagcagccg ccacactata ccacgtcggc actacagcag ccctgctgt | 3120 |
| ctcccacgcc gccagactat acaagacacc agcaggtacc ccacatcctt caaggactgc | 3180 |
| tttctccccg gcattcgctc accggccact cggacatccg gctgccccca acagagtttg | 3240 |
| cacagctcat taaaaggcag cagcaacaac ggcagcagca gcagcaacag cagcaacagc | 3300 |
| aagaatacca ggaactgttc aggcacatga accaagggga tgcggggagt ctggctccca | 3360 |
| gccttggggg acagagcatg acagagcgcc aggctttatc ttatcaaaat gctgactctt | 3420 |
| atcaccatca caccagcccc cagcatctgc tacaaatcag gcacaagaa tgtgtctcac | 3480 |
| aggcttcctc acccaccccg ccccacgggt atgctcacca gccggcactg atgcattcag | 3540 |
| agagcatgga ggaggactgc tcgtgtgagg gggccaagga tggcttccaa gacagtaaga | 3600 |
| gttcaagtac attgaccaaa ggttgccatg acagccctct gctcttgagt accggtggac | 3660 |
| ctggggaccc tgaatctttg ctaggaactg tgagtcatgc caagaattg gggatacatc | 3720 |
| cctatggtca tcagccaact gctgcattca gtaaaaataa ggtgcccagc agagagcctg | 3780 |
| tcatagggaa ctgcatggat agaagttctc caggacaagc agtggagctg ccggatcaca | 3840 |
| atgggctcgg gtacccagca cgcccctccg tccatgagca ccacaggccc cgggccctcc | 3900 |
| agagacacca cacgatccag aacagcgacg atgcttatgt acagctggat aacttgccag | 3960 |
| gaatgagtct cgtggctggg aaagcactta gctctgcccg gatgtcggat gcagttctca | 4020 |
| gtcagtcttc gctcatgggc agccagcagt ttcaggatgg ggaaaatgag gaatgtgggg | 4080 |
| caagcctggg aggtcatgag cacccagacc tgagtgatgg cagccagcat ttaaactcct | 4140 |
| cttgctatcc atctacgtgt attacagaca ttctgctcag ctacaagcac cccgaagtct | 4200 |
| ccttcagcat ggagcaggca ggcgtgtaac aagaaacaga gagttttgtg tacagcttgg | 4260 |
| gaatgaaaag gttgattgta aacccacagt atctagcagc gttgtgccaa attgcccttg | 4320 |
| tgtttctctc cacccaaaat atcacagctg ctttcctcac atttggttca tccgtgtgct | 4380 |
| gttcttttgg gttctgagag ggttttgcca tgtttgcttg tatgaccaag tcaccaagga | 4440 |
| aataaacagg aaggaaatcc | 4460 |

<210> SEQ ID NO 10
<211> LENGTH: 4919
<212> TYPE: DNA
<213> ORGANISM: Homo sapiens

<400> SEQUENCE: 10

| | |
|---|---|
| gagcaagcgg agcggccgtc gcccaagcca agccgcgctg ccaaccctcc cgcccgcccg | 60 |
| cgctcctgtc cgccgtgtct agcagcgggg cccagcatgg tcatggcgga tggcccgagg | 120 |
| cacttgcagc gcgggccggt ccgggtgggg ttctacgaca tcgagggcac gctgggcaag | 180 |
| ggcaacttcg ctgtggtgaa gctggggcgg caccggatca ccaagacgga ggtggcaata | 240 |
| aaaataatcg ataagtctca gctggatgca gtgaaccttg agaaaatcta ccgagaagta | 300 |
| caaataatga aaatgttaga ccaccctcac ataatcaaac tttatcaggt aatggagacc | 360 |
| aaaagtatgt tgtaccttgt gacagaatat gccaaaaatg gagaaatttt tgactatctt | 420 |
| gctaatcatg gccggttaaa tgagtctgaa gccaggcgaa aattctggca aatcctgtct | 480 |
| gctgttgatt attgtcatgg tcggaagatt gtgcaccgtg acctcaaagc tgaaaatctc | 540 |

```
ctgctggata acaacatgaa tatcaaaata gcagatttcg gttttggaaa tttctttaaa    600
agtggtgaac tgctggcaac atggtgtggc agccccctt atgcagcccc agaagtcttt    660
gaagggcagc agtatgaagg accacagctg acatctgga gtatgggagt tgttctttat    720
gtccttgtct gtggagctct gcccttttgat ggaccgactc ttccaatttt gaggcagagg    780
gttctggaag gaagattccg gattccgtat tcatgtcag aagattgcga gcaccttatc    840
cgaaggatgt tggtcctaga cccatccaaa cggctaacca tagcccaaat caaggagcat    900
aaatggatgc tcatagaagt tcctgtccag agacctgttc tctatccaca agagcaagaa    960
aatgagccat ccatcgggga gtttaatgag caggttctgc gactgatgca cagccttgga   1020
atagatcagc agaaaaccat tgagtctttg cagaacaaga gctataacca ctttgctgcc   1080
atttatttct tgttggtgga gcgcctgaaa tcacatcgga gcagtttccc agtggagcag   1140
agacttgatg ccgccagcg tcggcctagc accattgctg agcaaacagt tgccaaggca   1200
cagactgtgg ggctcccagt gaccatgcat tcaccgaaca tgaggctgct gcgatctgcc   1260
ctcctcccc aggcatccaa cgtggaggcc ttttcatttc cagcatctgg ctgtcaggcg   1320
gaagctgcat tcatggaaga agagtgtgtg gacactccaa aggtcaatgg ctgtctgctt   1380
gaccctgtgc ctcctgtcct ggtgcggaag ggatgccagt cactgcccag caacatgatg   1440
gagacctcca ttgacgaagg gctggagaca aaggagagg ccgaggaaga ccccgctcat   1500
gcctttgagg catttcagtc cacacgcagc gggcagagac ggcacactct gtcagaagtg   1560
accaatcaac tggtcgtgat gcctgggca gggaaaattt tctccatgaa tgacagcccc   1620
tcccttgaca gtgtggactc tgagtatgat atggggtctg ttcagaggga cctgaacttt   1680
ctggaagaca acccttccct taaggacatc atgttagcca atcagccttc accccgcatg   1740
acatctccct tcataagcct gagacctacc aacccagcca tgcaggctct gagctcccag   1800
aaacgagagg tccacaacag gtctccagtg agcttcagag agggccgcag agcatcagat   1860
acctccctca cccagggaat tgtagcattt agacaacatc ttcagaatct ggctagaacc   1920
aaaggaattc tagagttgaa caaagtgcag ttgttgtatg aacaaatagg accggaggca   1980
gaccctaacc tggcgccggc ggctcctcag ctccaggacc ttgctagcag ctgccctcag   2040
gaagaagttt ctcagcagca ggaaagcgtc tccactctcc ctgccagcgt gcatccccag   2100
ctgtccccac ggcagagcct ggagacccag tacctgcagc acagactcca gaagcccagc   2160
cttctgtcaa aggcccagaa cacctgtcag ctttattgca agaaccacc gcggagcctt   2220
gagcagcagc tgcaggaaca taggctccag cagaagcgac tctttcttca gaagcagtct   2280
caactgcagg cctatttaa tcagatgcag atagcagaga gctcctaccc acagccaagt   2340
cagcagctgc cccttccccg ccaggagact ccaccgcctt tcagcaggc cccaccgttc   2400
agcctgaccc agcccctgag ccccgtcctg gagccttcct ccgagcagat gcaatacagc   2460
cctttcctca gccagtacca agagatgcag cttcagcccc tgccctccac ttccggtccc   2520
cgggctgctc ctcctctgcc cacgcagcta cagcagcagc agccgccacc gccaccaccc   2580
cctccaccac cacgacagcc aggagctgcc ccagccccct acagttctc ctatcagact   2640
tgtgagctgc caagcgctgc ttcccctgcg ccagactatc ccactccctg tcagtatcct   2700
gtggatggag cccagcagag cgacctaacg gggccagact gtcccagaag cccaggactg   2760
caagaggccc cctccagcta cgacccacta gccctctctg agctacctgg actctttgat   2820
tgtgaaatgc tagcgctgt ggatccacaa cacaacgggg atgtcctggt gaattagtct   2880
cagcacagga attgaggtgg gtcaggtgaa ggaagagtgt atgttcctat ttttattcca   2940
```

```
gccttttaaa tttaaagctt attttcttgc cctctcccta acggggagaa atcgagccac    3000
ccaactggaa tcagagggtc tggctggggt ggatgttgct tcctcctggt tctgccccac    3060
cacaaagttt tctgtggcaa gtgctggaac atagttgtag gctgaggctc ctgcccttcg    3120
gtcgagtgga gcaagctctc gagggcagca ctgacaaatg tgttcctaag aagacattca    3180
gacccaggtg ttatgcagga ttacatccgt ttattatcaa gggcaacctt ggtgaaagca    3240
gaaagggtgt gtgctattgc atatatatgg gggaaaaggc aatatatttt tcactgaagc    3300
tgagcaacca catattgcta caaggcaaat caagaagaca tcaggaaatc agatgcacag    3360
gaaataaagg aaagctgtgc tttgtcattg aatcctaagt tcttagctgc tgatgcaagt    3420
tgtcccccaa ggccatcaca aagcagtggg gcatgagctg tgtttcaggg gccactaaat    3480
aacagctggt actgacccca gaaaccgcct tcatctccat tcggaagcag gtgacacacc    3540
ccttcagaag gtgccctggg ttgccgagtg tcagaatata ctcaggactc cagaggtgtc    3600
acacgtggaa ctgacaggag acccgccacc gtggaggcag ggggcaagaa actcaagaac    3660
gcatcaagag caccagccct gggccaggga agacaggctc ttcctgcagt ttctcgtgga    3720
cactgctggc ttgcgggcag tcggtctcca gggtacctgt tgtctctttt ccgatgtaat    3780
aactactttg accttacact atatgttgct agtagtttat tgagctttgt atatttggac    3840
agtttcatat agggcttaga gattttaagg acatgataaa tgaactttc tgtcccatgt     3900 gaagtggtag tgcggtgcct ttcccccaga tcatgcttta attctttctt ttctgtagaa    3960
accaacagtt tccatttatg tcaatgctaa atccaaagtc acttcagagt ttgttttcca    4020
ccatgtggga atcagcattc ttaatttcgt taaagttttg acttgtaatg aaatgttcaa    4080
gtattacagc aatattcaaa gaaagaacca cagatgtgtt aaccatttaa gcagatcatc    4140
tgccaaacat tatattacta ataaaactta accaacactt acaattcagt catcaaagta    4200
agtaaaaatt agatgctaca gctagctaac tgtatcccta gaaatgatga ataatttgcc    4260
atttggacag ttaacatcca ggtgttacaa agtcagtgtt aattctaaag atgatcattt    4320
ctgcccttta gaatggcttg tcccatcagc agatgaatgt gttaagcaca aagcatcttc    4380
cttaaagcac aaagagaggg actaactgat gctgcatcta gaaaacacct ttaagttgcc    4440
tttcctcttt gtagttagcg ttcaggcagg tgacgtgtgg aaagtctagg gggttccatt    4500
ctggccatgc gagcccagct cctaccaacg tcggtaactt gagcagtccc tgttgctggc    4560
cagagactgc ctggtcgcca gcgctcacca tgggtgccag gatgcttcgc agaggcactg    4620
tgctcacggt tggacttggt gtcagtggga aagggcagtg tggggactgt catttttgtg    4680
atttaataac acacagtgaa aatccaggaa gaatgaatta agcttcttct gggagttgtt    4740
tattcctgct cgtgcttaag attgatgatt tcgtgaaata aagaacatca tttcatttaa    4800
gagatcattt cattaagatc tctaatctgt tttgagtctt tacaaaatag ccagttataa    4860 aatgggctt gatttgttta gactgaagga agacgttttc ccaaaatata ctacagaag     4919
```

<210> SEQ ID NO 11
<211> LENGTH: 4919
<212> TYPE: DNA
<213> ORGANISM: Homo sapiens

<400> SEQUENCE: 11

```
gagcaagcgg agcggccgtc gcccaagcca agccgcgctg ccaaccctcc cgcccgcccg      60
cgctcctgtc cgccgtgtct agcagcgggg cccagcatgg tcatggcgga tggcccgagg    120
cacttgcagc gcgggccggt ccgggtgggg ttctacgaca tcgagggcac gctgggcaag    180
```

```
ggcaacttcg ctgtggtgaa gctggggcgg caccggatca ccaagacgga ggtggcaata    240
aaaataatcg ataagtctca gctggatgca gtgaaccttg agaaaatcta ccgagaagta    300
caaataatga aaatgttaga ccaccctcac ataatcaaac tttatcaggt aatggagacc    360
aaaagtatgt tgtaccttgt gacagaatat gccaaaaatg gagaaatttt tgactatctt    420
gctaatcatg gccggttaaa tgagtctgaa gccaggcgaa aattctggca atcctgtct     480 gctgttgatt attgtcatgg tcggaagatt gtgcaccgtg acctcaaagc tgaaaatctc    540
ctgctggata caacatgaa tatcaaaata gcagatttcg gttttggaaa tttctttaaa     600
agtggtgaac tgctggcaac atggtgtggc agccccccctt atgcagcccc agaagtcttt    660
gaagggcagc agtatgaagg accacagctg gacatctgga gtatgggagt tgttctttat    720
gtccttgtct gtggagctct gccctttgat ggaccgactc ttccaatttt gaggcagagg    780
gttctggaag gaagattccg gattccgtat ttcatgtcag aagattgcga gcaccttatc    840
cgaaggatgt tggtcctaga cccatccaaa cggctaacca tagcccaaat caaggagcat    900
aaatggatgc tcatagaagt tcctgtccag agacctgttc tctatccaca gagcaagaa     960 aatgagccat ccatcgggga gtttaatgag caggttctgc gactgatgca cagccttgga    1020
atagatcagc agaaaaccat tgagtctttg cagaacaaga gctataacca ctttgctgcc    1080
atttatttct tgttggtgga gcgcctgaaa tcacatcgga gcagtttccc agtggagcag    1140
agacttgatg gccgccagcg tcggcctagc accattgctg agcaaacagt tgccaaggca    1200
cagactgtgg ggctcccagt gaccatgcat tcaccgaaca tgaggctgct gcgatctgcc    1260
ctcctccccc aggcatccaa cgtggaggcc ttttcatttc agcatctgg ctgtcaggcg      1320 gaagctgcat tcatggaaga agagtgtgtg gacactccaa aggtcaatgg ctgtctgctt    1380
gaccctgtgc ctcctgtcct ggtgcggaag ggatgccagt cactgcccag caacatgatg    1440
gagacctcca ttgacgaagg gctggagaca aaggagagg ccgaggaaga ccccgctcat      1500
gcctttgagg catttcagtc cacacgcagc gggcagagac ggcacactct gtcagaagtg    1560
accaatcaac tggtcgtgat gcctggggca gggaaaattt tctccatgaa tgacagcccc    1620
tcccttgaca gtgtggactc tgagtatgat atggggtctg ttcagaggga cctgaacttt    1680
ctggaagaca acccttccct taaggacatc atgttagcca atcagccttc accccgcatg    1740
acatctccct tcataagcct gagacctacc aacccagcca tgcaggctct gagctcccag    1800
aaacgagagg tccacaacag gtctccagtg agcttcagag agggccgcag agcatcagat    1860
acctccctca cccagggaat tgtagcattt agacaacatc ttcagaatct ggctagaacc    1920
aaaggaattc tagagttgaa caaagtgcag ttgttgtatg aacaaatagg accggaggca    1980
gaccctaacc tggcgccggc ggctcctcag ctccaggacc ttgctagcag ctgccctcag    2040
gaagaagttt ctcagcagca ggaaagcgtc tccactctcc ctgccagcgt gcatccccag    2100
ctgtccccac ggcagagcct ggagacccag tacctgcagc acagactcca gaagcccagc    2160
cttctgtcaa aggcccagaa cacctgtcag ctttattgca agaaccacc gcggagcctt      2220 gagcagcagc tgcaggaaca taggctccag cagaagcgac tctttcttca gaagcagtct    2280
caactgcagg cctattttaa tcagatgcag atagcagaga gctcctaccc acagccaagt    2340
cagcagctgc cccttcccg ccaggagact ccaccgcctt tcagcaggc cccaccgttc       2400 agcctgaccc agccctgag ccccgtcctg gagccttcct ccgagcagat gcaatacagc     2460
cctttcctca gccagtacca agagatgcag cttcagcccc tgccctccac ttccggtccc    2520
cgggctgctc ctcctctgcc cacgcagcta cagcagcagc agccgccacc gccaccaccc    2580
```

```
cctccaccac cacgacagcc aggagctgcc ccagccccct tacagttctc ctatcagact    2640
tgtgagctgc caagcgctgc ttccctgcg  ccagactatc ccactccctg tcagtatcct    2700
gtggatggag cccagcagag cgacctaacg gggccagact gtcccagaag cccaggactg    2760
caagaggccc cctccagcta cgacccacta gccctctctg agctacctgg actctttgat    2820
tgtgaaatgc tagacgctgt ggatccacaa cacaacgggt atgtcctggt gaattagtct    2880
cagcacagga attgaggtgg gtcaggtgaa ggaagagtgt atgttcctat ttttattcca    2940
gccttttaaa tttaaagctt attttcttgc cctctcccta acggggagaa atcgagccac    3000
ccaactggaa tcagagggtc tggctggggt ggatgttgct tcctcctggt tctgccccac    3060
cacaaagttt tctgtggcaa gtgctggaac atagttgtag gctgaggctc ctgcccttcg    3120
gtcgagtgga gcaagctctc gagggcagca ctgacaaatg tgttcctaag aagacattca    3180
gacccaggtc ttatgcagga ttacatccgt ttgttatcaa gggcaacctt ggtgaaagca    3240
gaaagggtgt gtgctattgc atatatatgg gggaaaaggc aatatatttt tcactgaagc    3300
tgagcaacca catattgcta caaggcaaat caagaagaca tcaggaaatc agatgcacag    3360
gaaataaagg aaagctgtgc tttgtcattg aatcctaagt tcttagctgc tgatgcaagt    3420
tgtcccccaa ggccatcaca aagcagtggg gcatgagctg tgtttcaggg gccactaaat    3480
aacagctggt actgacccca gaaaccgcct tcatctccat tcggaagcag gtgacacacc    3540
ccttcagaag gtgccctggg ttgccgagtg tcagaatata ctcaggactc cagaggtgtc    3600
acacgtggaa ctgacaggag acccgccacc gtggaggcag ggggcaagaa actcaagaac    3660
gcatcaagag caccagccct gggccaggga agacaggctc ttcctgcagt ttctcgtgga    3720
cactgctggc ttgcgggcag tcggtctcca gggtacctgt tgtctctttt ccgatgtaat    3780
aactactttg accttacact atatgttgct agtagtttat tgagctttgt atatttggac    3840
agtttcatat agggcttaga gattttaagg acatgataaa tgaacttttc tgtcccatgt    3900
gaagtggtag tgcggtgcct ttcccccaga tcatgcttta attctttctt ttctgtagaa    3960
accaacagtt tccatttatg tcaatgctaa atccaaagtc acttcagagt ttgttttcca    4020
ccatgtggga atcagcattc ttaatttcgt taaagttttg acttgtaatg aaatgttcaa    4080
gtattacagc aatattcaaa gaagaaccca cagatgtgtt aaccatttaa gcagatcatc    4140
tgccaaacat tatattacta ataaaactta accaacactt acaattcagt catcaaagta    4200
agtaaaaatt agatgctaca gctagctaac tgtatcccta gaaatgatga ataatttgcc    4260
atttggacag ttaacatcca ggtgttacaa agtcagtgtt aattctaaag atgatcattt    4320
ctgcccttta gaatggcttg tcccatcagc agatgaatgt gttaagcaca aagcatcttc    4380
cttaaagcac aaagagaggg actaactgat gctgcatcta gaaaacacct ttaagttgcc    4440
tttcctcttt gtagttagcg ttcaggcagg tgacgtgtgg aaagtctagg gggttccatt    4500
ctggccatgc gagcccagct cctaccaacg tcggtaactt gagcagtccc tgttgctggc    4560
cagagactgc ctggtcgcca gcgctcacca tgggtgccag gatgcttcgc agaggcactg    4620
tgctcacggt tggacttggt gtcagtggga agggcagtg  tggggactgt catttttgtg    4680
atttaataac acacagtgaa aatccaggaa gaatgaatta agcttcttct gggagttgtt    4740
tattcctgct cgtgcttaag attgatgatt tcgtgaaata aagaacatca tttcatttaa    4800
gagatcattt cattaagatc tctaatctgt tttgagtctt tacaaaatag ccagttataa    4860
aatggggctt gatttgttta gactgaagga agacgttttc ccaaaatata ctacagaag    4919
```

<210> SEQ ID NO 12

<211> LENGTH: 8991
<212> TYPE: DNA
<213> ORGANISM: Homo sapiens

<400> SEQUENCE: 12

| | | | | | |
|---|---|---|---|---|---|
| gttggcctac | tggagccgcg | ctgccaaccc | tcccgcccgc | ccgcgctcct | gtccgccgtg | 60 |
| tctagcagcg | gggcccagca | tggtcatggc | ggatggcccg | aggcacttgc | agcgcgggcc | 120 |
| ggtccgggtg | gggttctacg | acatcgaggg | cacgctgggc | aagggcaact | tcgctgtggt | 180 |
| gaagctgggg | cggcaccgga | tcaccaagac | ggaggtggca | ataaaaataa | tcgataagtc | 240 |
| tcagctggat | gcagtgaacc | ttgagaaaat | ctaccgagaa | gtacaaataa | tgaaaatgtt | 300 |
| agaccaccct | cacataatca | aactttatca | ggtaatggag | accaaaagta | tgttgtacct | 360 |
| tgtgacagaa | tatgccaaaa | atggagaaat | ttttgactat | cttgctaatc | atggccggtt | 420 |
| aaatgagtct | gaagccaggc | gaaaattctg | gcaaatcctg | tctgctgttg | attattgtca | 480 |
| tggtcggaag | attgtgcacc | gtgacctcaa | agctgaaaat | ctcctgctgg | ataacaacat | 540 |
| gaatatcaaa | atagcagatt | tcggttttgg | aaatttcttt | aaaagtggtg | aactgctggc | 600 |
| aacatggtgt | ggcagccccc | cttatgcagc | cccagaagtc | tttgaagggc | agcagtatga | 660 |
| aggaccacag | ctggacatct | ggagtatggg | agttgttctt | tatgtccttg | tctgtggagc | 720 |
| tctgcccttt | gatggaccga | ctcttccaat | tttgaggcag | agggtctgg | aaggaagatt | 780 |
| ccggattccg | tatttcatgt | cagaagattg | cgagcacctt | atccgaagga | tgttggtcct | 840 |
| agacccatcc | aaacggctaa | ccatagccca | aatcaaggag | cataaatgga | tgctcataga | 900 |
| agttcctgtc | cagagacctg | ttctctatcc | acaagagcaa | gaaaatgagc | catccatcgg | 960 |
| ggagtttaat | gagcaggttc | tgcgactgat | gcacagcctt | ggaatagatc | agcagaaaac | 1020 |
| cattgagtct | ttgcagaaca | agagctataa | ccactttgct | gccatttatt | tcttgttggt | 1080 |
| ggagcgcctg | aaatcacatc | ggagcagttt | cccagtggag | cagagacttg | atggccgcca | 1140 |
| gcgtcggcct | agcaccattg | ctgagcaaac | agttgccaag | gcacagactg | tggggctccc | 1200 |
| agtgaccatg | cattcaccga | acatgaggct | gctgcgatct | gccctcctcc | cccaggcatc | 1260 |
| caacgtggag | gccttttcat | ttccagcatc | tggctgtcag | gcggaagctg | cattcatgga | 1320 |
| agaagagtgt | gtggacactc | caaaggtcaa | tggctgtctg | cttgaccctg | tgcctcctgt | 1380 |
| cctggtgcgg | aagggatgcc | agtcactgcc | cagcaacatg | atggagacct | ccattgacga | 1440 |
| agggctggag | acagaaggag | aggccgagga | agaccccgct | catgcctttg | aggcatttca | 1500 |
| gtccacacgc | agcgggcaga | gacggcacac | tctgtcagaa | gtgaccaatc | aactggtcgt | 1560 |
| gatgcctggg | gcagggaaaa | ttttctccat | gaatgacagc | ccctcccttg | acagtgtgga | 1620 |
| ctctgagtat | gatatggggt | ctgttcagag | ggacctgaac | tttctggaag | acaacccttc | 1680 |
| ccttaaggac | atcatgttag | ccaatcagcc | ttcaccccgc | atgacatctc | ccttcataag | 1740 |
| cctgagacct | accaacccag | ccatgcaggc | tctgagctcc | cagaaacgag | aggtccacaa | 1800 |
| caggtctcca | gtgagcttca | gagagggccg | cagagcatca | gatacctccc | tcacccaggg | 1860 |
| aattgtagca | tttagacaac | atcttcagaa | tctggctaga | accaaaggaa | ttctagagtt | 1920 |
| gaacaaagtg | cagttgttgt | atgaacaaat | aggaccggag | gcagaccta | acctggcgcc | 1980 |
| ggcggctcct | cagctccagg | accttgctag | cagctgccct | caggaagaag | tttctcagca | 2040 |
| gcaggaaagc | gtctccactc | tccctgccag | cgtgcatccc | cagctgtccc | cacggcagag | 2100 |
| cctggagacc | cagtacctgc | agcacagact | ccagaagccc | agccttctgt | caaaggccca | 2160 |
| gaacacctgt | cagctttatt | gcaaagaacc | accgcggagc | cttgagcagc | agctgcagga | 2220 |

-continued

```
acataggctc cagcagaagc gactctttct tcagaagcag tctcaactgc aggcctattt    2280
taatcagatg cagatagcag agagctccta cccacagcca gtcagcagc tgccccttcc     2340 ccgccaggag actccaccgc cttctcagca ggccccaccg ttcagcctga cccagcccct    2400 gagcccgtc ctggagcctt cctccgagca gatgcaatac agccctttcc tcagccagta    2460
ccaagagatg cagcttcagc ccctgccctc cacttccggt ccccgggctg ctcctcctct    2520
gcccacgcag ctacagcagc agcagccgcc accgccacca cccctccac caccacgaca    2580 gccaggagct gccccagccc ccttacagtt ctcctatcag acttgtgagc tgccaagcgc    2640
tgcttcccct gcgccagact atcccactcc ctgtcagtat cctgtggatg agcccagca    2700 gagcgaccta acggggccag actgtcccag aagcccagga ctgcaagagg cccctccag    2760 ctacgaccca ctagccctct ctgagctacc tggactcttt gattgtgaaa tgctagacgc    2820
tgtggatcca caacacaacg ggtatgtcct ggtgaattag tctcagcaca ggaattgagg    2880
tgggtcaggt gaaggaagag tgtatgttcc tattttatt ccagccttt aaatttaaag     2940 cttattttct tgccctctcc ctaacgggga gaaatcgagc cacccaactg gaatcagagg    3000
gtctggctgg ggtggatgtt gcttcctcct ggttctgccc caccacaaag ttttctgtgg    3060
caagtgctgg aacatagttg taggctgagg ctcctgccct tcggtcgagt ggagcaagct    3120
ctcgagggca gcactgacaa atgtgttcct aagaagacat tcagacccag gtcttatgca    3180
ggattacatc cgtttattat caagggcaac cttggtgaaa gcagaagggg tgtgtgctat    3240
tgcatatata tgggggaaaa ggcaatatat ttttcactga agctgagcaa ccacatattg    3300
ctacaaggca aatcaagaag acatcaggaa atcagatgca caggaaataa aggaaagctg    3360
tgctttgtca ttgaatccta agttcttagc tgctgatgca agttgtcccc caaggccatc    3420
acaaagcagt ggggcatgag ctgtgtttca ggggccacta ataacagct ggtactgacc     3480 ccagaaaccg ccttcatctc cattcggaag caggtgacac ccccttcag aaggtgccct     3540 gggttgccga gtgtcagaat atactcagga ctccagaggt gtcacacgtg aactgacag    3600 gagacccgcc accgtggagg caggggggcaa gaaactcaag aacgcatcaa gagccaccagc  3660 cctgggccag ggaagacagg ctcttcctgc agtttctcgt ggacactgct ggcttgcggg    3720
cagtcggtct ccagggtacc tgttgtctct tttccgatgt aataactact ttgaccttac    3780
actatatgtt gctagtagtt tattgagctt tgtatatttg gacagtttca tatagggctt    3840
agagatttta aggacatgat aaatgaactt ttctgtccca tgtgaagtgg tagtgcggtg    3900
cctttccccc agatcatgct ttaattcttt cttttctgta gaaaccaaca gtttccattt    3960
atgtcaatgc taaatccaaa gtcacttcag agtttgtttt ccaccatgtg ggaatcagca    4020
ttcttaattt cgttaaagtt ttgacttgta atgaaatgtt caagtattac agcaatattc    4080
aaagaaagaa ccacagatgt gttaaccatt taagcagatc atctgccaaa cattatatta    4140
ctaataaaac ttaaccaaca cttacaattc agtcatcaaa gtaagtaaaa attagatgct    4200
acagctagct aactgtatcc ctagaaatga tgaataattt gccatttgga cagttaacat    4260
ccaggtgtta caaagtcagt gttaattcta aagatgatca tttctgccct ttagaatggc    4320
ttgtcccatc agcagatgaa tgtgttaagc acaaagcatc ttccttaaag cacaaagaga    4380
gggactaact gatgctgcat ctagaaaaca cctttaagtt gcctttcctc tttgtagtta    4440
gcgttcaggc aggtgacgtg tggaaagtct aggggggttcc attctggcca tgcgagccca   4500
gctcctacca acgtcggtaa cttgagcagt ccctgttgct ggccagagac tgcctggtcg    4560
ccagcgctca ccatgggtgc caggatgctt cgcagaggca ctgtgctcac ggttggactt    4620
```

```
ggtgtcagtg ggaaagggca gtgtggggac tgtcattttt gtgatttaat aacacacagt   4680
gaaaatccag gaagaatgaa ttaagcttct tctgggagtt gtttattcct gctcgtgctt   4740
aagattgatg atttcgtgaa ataaagaaca tcatttcatt taagagatca tttcattaag   4800
atctctaatc tgttttgagt ctttacaaaa tagccagtta taaaatgggg cttgatttgt   4860
ttagactgaa ggaagacgtt ttcccaaaat atactacaga agtgctacaa tatttgcgat   4920
attaaaatgc ctgcagattg aaaatggggg ccactcattt cagaactgca ggaatggtgt   4980
agttacagat cgacataaac tcctgccccc caacaatgcc atgagctgct tagcccagga   5040
gacctgggag ctatggcagg acggttaggc cagccgatga gggactgcag agaggctact   5100
ggaaggttaa ggacccagag agaaatcgag aggtgcccta cggcagccag gcctatcagg   5160
atccgtcaca cacggcagcg gcgtggacac cggcctgatg cagagcgtga cccctcctgc   5220
tgggacctgt gttgtaagct cctatttgct tatcttgttt atttcaagca gaaatcaata   5280
aattccataa ccctctgtat tgactgcaat gtaagctgct gaggagactg gttctgttgg   5340
tcagtcaggt gtttgctcag ccctgtctga tcacctgtgc tgctctgtcc ctaactagtg   5400
acccatggaa gcttccaagc agttttctct tcatcactac taacaaacga aacactaaga   5460
aggcttagta tcgctctttt tctgcggggc tactctgaag tactgacttg ctttccagtc   5520
tgattcacgt tagcagtgtg tacactactg tatcatcatc agcttcatca ccctgtaaac   5580
caggctcctc tgaagagact ttggtgagat gaacgtgagg taaaaatttc gttcggcaaa   5640
aagtgcaata tgtgtggtac tttatttttt atgttctttt tttaaatctg ggtattagt    5700 ctgtgctttg ggagaaatgc actagctctg caattcccag ctgggcaagt gtgtctctag   5760
tatctccagc aactgataca ctggtccctg taaggcaaac agcatgttag cccgacagga   5820 agaggggggcc cactttcaca ttcccggtga cactgaccgt ccccagctgc cccctcgcca   5880
cctctgcctg cactgccttc tgtcaccgtg ggaaaaggag gctgatggtt ctctacacca   5940
tccaccttga gaatccctgc gtgggagagc atcagggccc accaggggag tggggatggg   6000
gctcaggggc tgttcatgcc catctgagca aaccccttct ctcttccatc cacttttgcc   6060
tcctaggaaa gaaaaagtca gtggcccttt cttcctcaga tatcaagaac tcccaagtgt   6120
ttaaaccgta tgctggagtc agtggttggg acagacagga gcccaagact gaagccagcc   6180
cttgcctctt gtgtcccttc ccaactctgg tgctggagta atggggtgct ctgcattttg   6240
atggggagca aggggggacc ccccctgtag gagtatcggc ctctcccctg cccctaccc    6300 tctctcgtgg accaaagtct ccagcagaag ggactcatca taagactgac gactccccca   6360
cctccaccca cacccgagt gtcatcagtc ctaaaggcag ggaaacgctc acagaattct    6420
gcccacgggt tagatgtggg gagaaggata ttctcagctc cagagtgatt aggtgatcag   6480
ccagaaacta aggcaaggtg acaagcagca gcctggagtc acagttggtc ccaggcgtgt   6540
gggcactaag cagcctctgg agacatgcgg gcagttgagg atgcaaggac acagtgagtg   6600
agtggcgctc cttttttgggg tcctccagcc tctagtcaag ccccaggttc gtaaatatgt   6660
ttgtattaca ttttaaaacc tgtatcaaca gtcacattta agctccctat tggtttaaag   6720
aaaattcgta ctccaggtaa cttttttccca ttcgacctcc tatagagaca atatgcagtg   6780
tgtcatttca cagtctcagt ccctgtgaac agtggctgac accggtgcca gggctgacct   6840
gctacactca aactcctaaa ctgggctgcc tctaactgcc tcctgggaag ccacccgagc   6900
cactcggtct ctttgtgcct aaacatgaaa ggtgaaaatt ggagaacagg gaagctcgta   6960
agttggagtc attgtacagg cagggatctt tgatcatttt gttgcttctg gaatttattt   7020
```

```
aatttttttt tttttgagac agagcgagac tccacctcaa aaaaaaaaaa aaaaagacaa    7080
gagcagtatc atctgcctct gtttctaaac tggacaaaga gattttctta aagtttctat    7140
catctccctt ctgacaggtt ctacagtgtg gtctgaagca cctgtaatgt cagagccctt    7200
gtctggccct tggtgcaggt gaacgaaag cagtggagcc tctcaccttc cagtagcctc    7260
tcacattctt attttaccat ttttgtccta attaaggtag cctagctgat tctagaagac    7320
agccatccta cgtgcacccc caccttgtgt ccacatcttc tccaggcagg tttcaaccta    7380
tcagcagact caggcacaca ctggggcaca gatagagaac caggcggcag cagtgctcgc    7440
agacccaccc agggagagct gtgatgggtt ctgcccagat actctgctcg cccacccaca    7500
agggagcaat agcttatatt tgtacattag ttttaccaag cactttctct tctaaccctc    7560
acaacaattc tatgaaatta gctggggaga tactgtcctt attttcaca gctgaagaaa    7620 ccaaagcttt gggaagtttg tgacttctct gagatcacag ctggtgatag aaggagctgg    7680
gacacgcgct tgggttgact ggcttctggt tttggttctc tggcttctag tgctggaaga    7740
agccctctct ttcccttctc tttcctcagt agcatctgac tcttttcata agcaaacagc    7800
tgtataaaca aagcccccat tttggtcaag cacagggtga atgtgatatt gttcccacaa    7860
ccttattctc cactcaacag ccgcctggct ttggggaaga ggccgccttc aggtgacagt    7920
gcagctgtcc aggtggccgt gcactgaacc aggctgaggg agacaaaaac ccgcagacc    7980 cgcctgcctt tcagcgtcca gttaactgca gaagtttagg ctcacctcaa agatgtctag    8040 ttttccaag ttacaataca gcagtttcct acagaacacc cccttcctca attgccaagg    8100
ggccgcatcg cacggcatca ggccaccact gcaggccagc agattccacc ccaggaacgg    8160
tcatgaactc agcctttgtc tcaacgaggg gcgtaacatt tccttacagt caagccccat    8220
caactagaag tgcttattac ttttaggatt aaaaaagtaa taacagactt tgacttaata    8280
ctctgtcttt tcagaggcaa agtgggtggg tagaggggag ctttaaaaat agaagtacaa    8340
aacaacatcc tggaaacata tgaccccaga tggaataatg tcacattccc cagtgcagat    8400
aatgggctgc tgctggctct gtggtgtctg tctgcagaag atttgctcag tcaaggaaat    8460
tcaagtggtg agacctttcc accatggggtg gtaagagaaa cctgccttca ccaaaatctc    8520
tgaaggggaa agaagtggag agaaaggttt gcttcacttc ggggactgca gtttgagaaa    8580
taaaagggat acagagatat ctgcactttg tagaaagggc aagattattt gcttatatct    8640
gaagggaggt gggtggtttt gctggatgtt tggtctgaaa gagttacttt tgataaagtt    8700
aatctaattg tagttatatt ttctgtgtgc ttttttttaa ttactaagaa aaaaattggt    8760
gagttcagta gctttggtat tatgagtgca aatcataata gctccaatgt gaaaaaaaaa    8820
atcaaaagta taacttgtca cttaatgtta gaaaattgcc taaaatgcag tgtaataaat    8880
aatctctgta ccaaatagta atttaaatgg ggtaattttc tgcaaggaaa atgtactgtt    8940
tttatgtttc caaccctctt gaattaaaat aaaaacaact tctttctaa g             8991
```

<210> SEQ ID NO 13
<211> LENGTH: 5694
<212> TYPE: DNA
<213> ORGANISM: Homo sapiens

<400> SEQUENCE: 13

```
gggaaggagc gaaggagcga aggagcaagc ggagcggccg tcgcccaagc caagccgcgc      60
tgccaaccct cccgcccgcc cgcgctcctg tccgccgtgt ctagcagcgg ggcccagcat     120
ggtcatggcg gatggcccga ggcacttgca gcgcgggccg gtccgggtgg ggttctacga     180
```

```
catcgagggc acgctgggca agggcaactt cgctgtggtg aagctggggc ggcaccggat    240
caccaagacg gaggtggcaa taaaataat cgataagtct cagctggatg cagtgaacct     300
tgagaaaatc taccgagaag tacaaataat gaaaatgtta gaccaccctc acataatcaa    360
actttatcag gtaatggaga ccaaaagtat gttgtacctt gtgacagaat atgccaaaaa    420
tggagaaatt tttgactatc ttgctaatca tggccggtta aatgagtctg aagccaggcg    480
aaaattctgg caaatcctgt ctgctgttga ttattgtcat ggtcggaaga ttgtgcaccg    540
tgacctcaaa gctgaaaatc tcctgctgga taacaacatg aatatcaaaa tagcagattt    600
cggttttgga aatttcttta aaagtggtga actgctggca acatggtgtg gcagccccc    660
ttatgcagcc ccagaagtct ttgaagggca gcagtatgaa ggaccacagc tggacatctg    720
gagtatggga gttgttcttt atgtccttgt ctgtggagct ctgcccttg atggaccgac    780
tcttccaatt ttgaggcaga gggttctgga aggaagattc cggattccgt atttcatgtc    840
agaagattgc gagcacctta tccgaaggat gttggtccta gacccatcca aacggctaac    900
catagcccaa atcaaggagc ataaatggat gctcatagaa gttcctgtcc agagacctgt    960
tctctatcca caagagcaag aaaatgagcc atccatcggg gagtttaatg agcaggttct   1020
gcgactgatg cacagccttg aatagatca gcagaaaacc attgagtctt tgcagaacaa    1080
gagctataac cactttgctg ccatttattt cttgttggtg gagcgcctga atcacatcg    1140
gagcagtttc ccagtggagc agagacttga tggccgccag cgtcggccta gcaccattgc    1200
tgagcaaaca gttgccaagg cacagactgt ggggctccca gtgaccatgc attcaccgaa    1260
catgaggctg ctgcgatctg ccctcctccc ccaggcatcc aacgtggagg ccttttcatt    1320
tccagcatct ggctgtcagg cggaagctgc attcatggaa gaagagtgtg tggacactcc    1380
aaaggtcaat ggctgtctgc ttgaccctgt gcctcctgtc ctggtgcgga agggatgcca    1440
gtcactgccc agcaacatga tggagacctc cattgacgaa gggctggaga cagaaggaga    1500
ggccgaggaa gaccccgctc atgcctttga ggcatttcag tccacacgca gcgggcagag    1560
acggcacact ctgtcagaag tgaccaatca actggtcgtg atgcctgggg cagggaaaat    1620
tttctccatg aatgacagcc cctcccttga cagtgtggac tctgagtatg atatgggtc    1680
tgttcagagg gacctgaact ttctggaaga caacccttcc cttaaggaca tcatgttagc    1740
caatcagcct tcaccccgca tgacatctcc cttcataagc ctgagaccta ccaacccagc    1800
catgcaggct ctgagctccc agaaacgaga ggtccacaac aggtctccag tgagcttcag    1860
agagggccgc agagcatcag atacctccct cacccaggga attgtagcat ttagacaaca    1920
tcttcagaat ctggctagaa ccaaaggaat tctagagttg aacaaagtgc agttgttgta    1980
tgaacaaata ggaccggagg cagacctaa cctggcgccg gcggctcctc agctccagga    2040
ccttgctagc agctgccctc aggaagaagt ttctcagcag caggaaagcg tctccactct    2100
ccctgccagc gtgcatcccc agctgtcccc acgcagagc ctggagaccc agtacctgca    2160
gcacagactc cagaagccca gccttctgtc aaaggcccag aacacctgtc agctttattg    2220
caaagaacca ccgcggagcc ttgagcagca gctgcaggaa cataggctcc agcagaagcg    2280
actctttctt cagaagcagt ctcaactgca ggcctatttt aatcagatgc agatagcaga    2340
gagctcctac ccacagccaa gtcagcagct gcccccttccc cgccaggaga ctccaccgcc    2400
ttctcagcag gccccaccgt tcagcctgac ccagcccctg agcccgtcc tggagccttc    2460
ctccgagcag atgcaataca gcccttttcct cagccagtac caagagatgc agcttcagcc    2520
cctgcctcc acttccggtc cccgggctgc tcctcctctg cccacgcagc tacagcagca    2580
```

```
gcagccgcca ccgccaccac cccctccacc accacgacag ccaggagctg ccccagcccc    2640
cttacagttc tcctatcaga cttgtgagct gccaagcgct gcttccoctg cgccagacta    2700 tcccactccc tgtcagtatc ctgtggatgg agcccagcag agcgacctaa cggggccaga    2760
ctgtcccaga agcccaggac tgcaagaggc ccctccagc tacgacccac tagccctctc     2820
tgagctacct ggactctttg attgtgaaat gctagacgct gtggatccac aacacaacgg    2880
gtatgtcctg gtgaattagt ctcagcacag gaattgaggt gggtcaggtg aaggaagagt    2940
gtatgttcct attttattc cagccttta aatttaaagc ttattttctt gccctctccc      3000
taacggggag aaatcgagcc acccaactgg aatcagaggg tctggctggg gtggatgttg    3060
cttcctcctg gttctgcccc accacaaagt tttctgtggc aagtgctgga acatagttgt    3120
aggctgaggc tcctgcccctt cggtcgagtg gagcaagctc tcgagggcag cactgacaaa   3180
tgtgttccta agaagacatt cagacccagg tcttatgcag gattacatcc gtttattatc    3240
aagggcaacc ttggtgaaag cagaaagggt gtgtgctatt gcatatatat gggggaaaag    3300
gcaatatatt tttcactgaa gctgagcaac cacatattgc tacaaggcaa atcaagaaga    3360
catcaggaaa tcagatgcac aggaaataaa ggaaagctgt gctttgtcat tgaatcctaa    3420
gttcttagct gctgatgcaa gttgtccccc aaggccatca caaagcagtg gggcatgagc    3480
tgtgtttcag gggccactaa ataacagctg gtactgaccc cagaaaccgc cttcatctcc    3540
attcggaagc aggtgacaca ccccttcaga aggtgccctg ggttgccgag tgtcagaata    3600
tactcaggac tccagaggtg tcacacgtgg aactgacagg agacccgcca ccgtggaggc    3660 aggggcaag aaactcaaga acgcatcaag agcaccagcc ctgggccagg gaagacaggc     3720
tcttcctgca gtttctcgtg gacactgctg gcttgcgggc agtcggtctc cagggtacct    3780
gttgtctctt ttccgatgta ataactactt tgaccttaca ctatatgttg ctagtagttt    3840
attgagcttt gtatatttgg acagtttcat ataggctta gagattttaa ggacatgata    3900
aatgaacttt tctgtcccat gtgaagtggt agtgcggtgc ctttcccca gatcatgctt     3960 taattcttc ttttctgtag aaccaacag tttccattta tgtcaatgct aaatccaaag      4020
tcacttcaga gttgtttc caccatgtgg gaatcagcat tcttaatttc gttaaagttt      4080
tgacttgtaa tgaaatgttc aagtattaca gcaatattca agaaagaac cacagatgtg     4140 ttaaccattt aagcagatca tctgccaaac attatattac taataaaact taaccaacac    4200
ttacaattca gtcatcaaag taagtaaaaa ttagatgcta cagctagcta actgtatccc    4260
tagaaatgat gaataattg ccatttggac agttaacatc caggtgttac aaagtcagtg     4320
ttaattctaa agatgatcat ttctgcccctt tagaatggct tgtcccatca gcagatgaat   4380
gtgttaagca caaagcatct tccttaaagc acaaagagag ggactaactg atgctgcatc    4440
tagaaaacac ctttaagttg cctttcctct tgtagttag cgttcaggca ggtgacgtgt     4500
ggaaagtcta gggggttcca ttctggccat gcgagcccag ctcctaccaa cgtcggtaac    4560
ttgagcagtc cctgttgctg ccagagact gcctggtcgc cagcgctcac catgggtgcc     4620
aggatgcttc gcagaggcac tgtgctcacg gttggacttg gtgtcagtgg gaaagggcag    4680
tgtggggact gtcattttttg tgattaata acacacagtg aaaatccagg aagaatgaat    4740
taagcttctt ctgggagttg tttattcctg ctcgtgctta agattgatga tttcgtgaaa    4800
taaagaacat catttcattt aagagatcat ttcattaaga tctctaatct gttttgagtc    4860
tttacaaaat agccagttat aaaatggggc ttgatttgtt tagactgaag gaagacgttt    4920
tcccaaaata tactacagaa gtgctacaat atttgcgata ttaaaatgcc tgcagattga    4980
```

-continued

```
aaatgggggc cactcatttc agaactgcag gaatggtgta gttacagatc gacataaact      5040
cctgcccccc aacaatgcca tgagctgctt agcccaggag acctgggagc tatggcagga      5100
cggttaggcc agccgatgag ggactgcaga gaggctactg gaaggttaag gacccagaga      5160
gaaatcgaga ggtgccctac agcagccagg cctatcagga tccgtcacac acggcagcgg      5220
cgtggacacc ggcctgatgc agagcgtgac ccctcctgct gggacctgtg ttgtaagctc      5280
ctatttgctt atcttgttta tttcaagcag aaatcaataa attccataac cctctgtatt      5340
gactgcaatg taagctgctg aggagactgg ttctgttggt cagtcaggtg tttgctcagc      5400
cctgtctgat cacctgtgct gctctgtccc taactagtga cccatggaag cttccaagca      5460
gttttctctt catcactact aacaaacgaa acactaagaa ggcttagtat cgctctttt       5520 ctgcggggct actctgaagt actgacttgc tttccagtct gattcacgtt agcagtgtgt      5580
acactactgt atcatcatca gcttcatcac cctgtaaacc aggctcctct gaagagactt      5640
tggtgagatg aacgtgaggt aaaaatttcg ttcggcaaaa aaaaaaaaaa aaaa            5694
```

<210> SEQ ID NO 14
<211> LENGTH: 786
<212> TYPE: PRT
<213> ORGANISM: Homo sapiens

<400> SEQUENCE: 14

```
Met Val Ile Met Ser Glu Phe Ser Ala Asp Pro Ala Gly Gln Gly Gln
1               5                   10                  15

Gly Gln Gln Lys Pro Leu Arg Val Gly Phe Tyr Asp Ile Glu Arg Thr
                20                  25                  30

Leu Gly Lys Gly Asn Phe Ala Val Val Lys Leu Ala Arg His Arg Val
            35                  40                  45

Thr Lys Thr Gln Val Ala Ile Lys Ile Ile Asp Lys Thr Arg Leu Asp
        50                  55                  60

Ser Ser Asn Leu Glu Lys Ile Tyr Arg Glu Val Gln Leu Met Lys Leu
65                  70                  75                  80

Leu Asn His Pro His Ile Ile Lys Leu Tyr Gln Val Met Glu Thr Lys
                85                  90                  95

Asp Met Leu Tyr Ile Val Thr Glu Phe Ala Lys Asn Gly Glu Met Phe
            100                 105                 110

Asp Tyr Leu Thr Ser Asn Gly His Leu Ser Glu Asn Glu Ala Arg Lys
        115                 120                 125

Lys Phe Trp Gln Ile Leu Ser Ala Val Glu Tyr Cys His Asp His His
    130                 135                 140

Ile Val His Arg Asp Leu Lys Thr Glu Asn Leu Leu Leu Asp Gly Asn
145                 150                 155                 160

Met Asp Ile Lys Leu Ala Gly Thr Glu Asp Phe Gly Phe Gly Asn Phe
                165                 170                 175

Tyr Lys Ser Gly Glu Pro Leu Ser Thr Trp Cys Gly Ser Pro Pro Tyr
            180                 185                 190

Ala Ala Pro Glu Val Phe Glu Gly Lys Glu Tyr Glu Gly Pro Gln Leu
        195                 200                 205

Asp Ile Trp Ser Leu Gly Val Val Leu Tyr Val Leu Val Cys Gly Ser
    210                 215                 220

Leu Pro Phe Asp Gly Pro Asn Leu Pro Thr Leu Arg Gln Arg Val Leu
225                 230                 235                 240

Glu Gly Arg Phe Arg Ile Pro Phe Phe Met Ser Gln Asp Cys Glu Ser
                245                 250                 255
```

```
Leu Ile Arg Arg Met Leu Val Val Asp Pro Ala Arg Arg Ile Thr Ile
            260                 265                 270

Ala Gln Ile Arg Gln His Arg Trp Met Arg Ala Glu Pro Cys Leu Pro
        275                 280                 285

Gly Pro Ala Cys Pro Ala Phe Ser Ala His Ser Tyr Thr Ser Asn Leu
    290                 295                 300

Gly Asp Tyr Asp Glu Gln Ala Leu Gly Ile Met Gln Thr Leu Gly Val
305                 310                 315                 320

Asp Arg Gln Arg Thr Val Glu Ser Leu Gln Asn Ser Ser Tyr Asn His
                325                 330                 335

Phe Ala Ala Ile Tyr Tyr Leu Leu Leu Glu Arg Leu Lys Glu Tyr Arg
            340                 345                 350

Asn Ala Gln Cys Ala Arg Pro Gly Pro Ala Arg Gln Pro Arg Pro Arg
        355                 360                 365

Ser Ser Asp Leu Ser Gly Leu Glu Val Pro Gln Glu Gly Leu Ser Thr
    370                 375                 380

Asp Pro Phe Arg Pro Ala Leu Leu Cys Pro Gln Pro Gln Thr Leu Val
385                 390                 395                 400

Gln Ser Val Leu Gln Ala Glu Met Asp Cys Glu Leu Gln Ser Ser Leu
                405                 410                 415

Gln Trp Pro Leu Phe Phe Pro Val Asp Ala Ser Cys Ser Gly Val Phe
            420                 425                 430

Arg Pro Arg Pro Val Ser Pro Ser Ser Leu Leu Asp Thr Ala Ile Ser
        435                 440                 445

Glu Glu Ala Arg Gln Gly Pro Gly Leu Glu Glu Glu Asp Thr Gln
    450                 455                 460

Glu Ser Leu Pro Ser Ser Thr Gly Arg Arg His Thr Leu Ala Glu Val
465                 470                 475                 480

Ser Thr Arg Leu Ser Pro Leu Thr Ala Pro Cys Lys Phe Val Ser Pro
                485                 490                 495

Ser Thr Thr Ala Ser Pro Ala Glu Gly Thr Ser Ser Asp Ser Cys Leu
            500                 505                 510

Thr Phe Ser Ala Ser Lys Ser Pro Ala Gly Leu Ser Gly Thr Pro Ala
        515                 520                 525

Thr Gln Gly Leu Leu Gly Ala Cys Ser Pro Val Arg Leu Ala Ser Pro
    530                 535                 540

Phe Leu Gly Ser Gln Ser Ala Thr Pro Val Leu Gln Ala Gln Gly Gly
545                 550                 555                 560

Leu Gly Gly Ala Val Leu Leu Pro Val Ser Phe Gln Glu Gly Arg Arg
                565                 570                 575

Ala Ser Asp Thr Ser Leu Thr Gln Gly Leu Lys Ala Phe Arg Gln Gln
            580                 585                 590

Leu Arg Lys Thr Thr Arg Thr Lys Gly Phe Leu Gly Leu Asn Lys Ile
        595                 600                 605

Lys Gly Leu Ala Arg Gln Val Cys Gln Ala Pro Ala Ser Arg Ala Ser
    610                 615                 620

Arg Gly Gly Leu Ser Pro Phe His Ala Pro Ala Gln Ser Pro Gly Leu
625                 630                 635                 640

His Gly Gly Ala Ala Gly Ser Arg Glu Gly Trp Ser Leu Leu Glu Glu
                645                 650                 655

Val Leu Glu Gln Gln Arg Leu Leu Gln Leu Gln His Pro Ala Ala
            660                 665                 670

Ala Pro Gly Cys Ser Gln Ala Pro Gln Pro Ala Pro Ala Pro Phe Val
        675                 680                 685
```

```
Ile Ala Pro Cys Asp Gly Pro Gly Ala Ala Pro Leu Pro Ser Thr Leu
    690                 695                 700

Leu Thr Ser Gly Leu Pro Leu Pro Pro Leu Leu Gln Thr Gly
705                 710                 715                 720

Ala Ser Pro Val Ala Ser Ala Ala Gln Leu Leu Asp Thr His Leu His
                725                 730                 735

Ile Gly Thr Gly Pro Thr Ala Leu Pro Ala Val Pro Pro Arg Leu
                740                 745                 750

Ala Arg Leu Ala Pro Gly Cys Glu Pro Leu Gly Leu Leu Gln Gly Asp
            755                 760                 765

Cys Glu Met Glu Asp Leu Met Pro Cys Ser Leu Gly Thr Phe Val Leu
770                 775                 780

Val Gln
785

<210> SEQ ID NO 15
<211> LENGTH: 783
<212> TYPE: PRT
<213> ORGANISM: Homo sapiens

<400> SEQUENCE: 15

Met Val Ile Met Ser Glu Phe Ser Ala Asp Pro Ala Gly Gln Gly Gln
1               5                   10                  15

Gly Gln Gln Lys Pro Leu Arg Val Gly Phe Tyr Asp Ile Glu Arg Thr
            20                  25                  30

Leu Gly Lys Gly Asn Phe Ala Val Val Lys Leu Ala Arg His Arg Val
        35                  40                  45

Thr Lys Thr Gln Val Ala Ile Lys Ile Ile Asp Lys Thr Arg Leu Asp
    50                  55                  60

Ser Ser Asn Leu Glu Lys Ile Tyr Arg Glu Val Gln Leu Met Lys Leu
65                  70                  75                  80

Leu Asn His Pro His Ile Ile Lys Leu Tyr Gln Val Met Glu Thr Lys
                85                  90                  95

Asp Met Leu Tyr Ile Val Thr Glu Phe Ala Lys Asn Gly Glu Met Phe
            100                 105                 110

Asp Tyr Leu Thr Ser Asn Gly His Leu Ser Glu Asn Glu Ala Arg Lys
        115                 120                 125

Lys Phe Trp Gln Ile Leu Ser Ala Val Glu Tyr Cys His Asp His His
    130                 135                 140

Ile Val His Arg Asp Leu Lys Thr Glu Asn Leu Leu Leu Asp Gly Asn
145                 150                 155                 160

Met Asp Ile Lys Leu Ala Asp Phe Gly Phe Gly Asn Phe Tyr Lys Ser
                165                 170                 175

Gly Glu Pro Leu Ser Thr Trp Cys Gly Ser Pro Pro Tyr Ala Ala Pro
            180                 185                 190

Glu Val Phe Glu Gly Lys Glu Tyr Glu Gly Pro Gln Leu Asp Ile Trp
        195                 200                 205

Ser Leu Gly Val Val Leu Tyr Val Leu Val Cys Gly Ser Leu Pro Phe
    210                 215                 220

Asp Gly Pro Asn Leu Pro Thr Leu Arg Gln Arg Val Leu Glu Gly Arg
225                 230                 235                 240

Phe Arg Ile Pro Phe Phe Met Ser Gln Asp Cys Glu Ser Leu Ile Arg
                245                 250                 255

Arg Met Leu Val Val Asp Pro Ala Arg Arg Ile Thr Ile Ala Gln Ile
            260                 265                 270
```

```
Arg Gln His Arg Trp Met Arg Ala Glu Pro Cys Leu Pro Gly Pro Ala
        275                 280                 285

Cys Pro Ala Phe Ser Ala His Ser Tyr Thr Ser Asn Leu Gly Asp Tyr
    290                 295                 300

Asp Glu Gln Ala Leu Gly Ile Met Gln Thr Leu Gly Val Asp Arg Gln
305                 310                 315                 320

Arg Thr Val Glu Ser Leu Gln Asn Ser Ser Tyr Asn His Phe Ala Ala
                325                 330                 335

Ile Tyr Tyr Leu Leu Leu Glu Arg Leu Lys Glu Tyr Arg Asn Ala Gln
            340                 345                 350

Cys Ala Arg Pro Gly Pro Ala Arg Gln Pro Arg Pro Arg Ser Ser Asp
        355                 360                 365

Leu Ser Gly Leu Glu Val Pro Gln Glu Gly Leu Ser Thr Asp Pro Phe
    370                 375                 380

Arg Pro Ala Leu Leu Cys Pro Gln Pro Gln Thr Leu Val Gln Ser Val
385                 390                 395                 400

Leu Gln Ala Glu Met Asp Cys Glu Leu Gln Ser Ser Leu Gln Trp Pro
                405                 410                 415

Leu Phe Phe Pro Val Asp Ala Ser Cys Ser Gly Val Phe Arg Pro Arg
            420                 425                 430

Pro Val Ser Pro Ser Ser Leu Leu Asp Thr Ala Ile Ser Glu Glu Ala
        435                 440                 445

Arg Gln Gly Pro Gly Leu Glu Glu Gln Asp Thr Gln Glu Ser Leu
    450                 455                 460

Pro Ser Ser Thr Gly Arg Arg His Thr Leu Ala Glu Val Ser Thr Arg
465                 470                 475                 480

Leu Ser Pro Leu Thr Ala Pro Cys Ile Val Val Ser Pro Ser Thr Thr
                485                 490                 495

Ala Ser Pro Ala Glu Gly Thr Ser Ser Asp Ser Cys Leu Thr Phe Ser
            500                 505                 510

Ala Ser Lys Ser Pro Ala Gly Leu Ser Gly Thr Pro Ala Thr Gln Gly
        515                 520                 525

Leu Leu Gly Ala Cys Ser Pro Val Arg Leu Ala Ser Pro Phe Leu Gly
    530                 535                 540

Ser Gln Ser Ala Thr Pro Val Leu Gln Ala Gln Gly Gly Leu Gly Gly
545                 550                 555                 560

Ala Val Leu Leu Pro Val Ser Phe Gln Glu Gly Arg Arg Ala Ser Asp
                565                 570                 575

Thr Ser Leu Thr Gln Gly Leu Lys Ala Phe Arg Gln Gln Leu Arg Lys
            580                 585                 590

Thr Thr Arg Thr Lys Gly Phe Leu Gly Leu Asn Lys Ile Lys Gly Leu
        595                 600                 605

Ala Arg Gln Val Cys Gln Val Pro Ala Ser Arg Ala Ser Arg Gly Gly
    610                 615                 620

Leu Ser Pro Phe His Ala Pro Ala Gln Ser Pro Gly Leu His Gly Gly
625                 630                 635                 640

Ala Ala Gly Ser Arg Glu Gly Trp Ser Leu Leu Glu Glu Val Leu Glu
                645                 650                 655

Gln Gln Arg Leu Leu Gln Leu Gln His His Pro Ala Ala Ala Pro Gly
            660                 665                 670

Cys Ser Gln Ala Pro Gln Pro Ala Pro Ala Pro Phe Val Ile Ala Pro
        675                 680                 685

Cys Asp Gly Pro Gly Ala Ala Pro Leu Pro Ser Thr Leu Leu Thr Ser
```

-continued

```
            690                 695                 700
Gly Leu Pro Leu Leu Pro Pro Leu Gln Thr Gly Ala Ser Pro
705                 710                 715                 720

Val Ala Ser Ala Ala Gln Leu Leu Asp Thr His Leu His Ile Gly Thr
                725                 730                 735

Gly Pro Thr Ala Leu Pro Ala Val Pro Pro Arg Leu Ala Arg Leu
                740                 745                 750

Ala Pro Gly Cys Glu Pro Leu Gly Leu Gln Gly Asp Cys Glu Met
                755                 760                 765

Glu Asp Leu Met Pro Cys Ser Leu Gly Thr Phe Val Leu Val Gln
770                 775                 780

<210> SEQ ID NO 16
<211> LENGTH: 1371
<212> TYPE: PRT
<213> ORGANISM: Homo sapiens

<400> SEQUENCE: 16

Ala Gln Gly Trp Gln Ala Val Gly Thr Gly Ala Arg Ala Ser Ala Val
1               5                   10                  15

Ala Ala Val Pro Ser Val Ser Leu Leu Ser Gly Ala Ser Ser Ser
                20                  25                  30

Leu Ala Trp Cys Gly Leu Ala Thr Gly Ala Leu Gly Ala Gly Ala Arg
                35                  40                  45

Gly Ile Pro Glu Leu Arg Gly Ala Ala Gly Ala Gly Gly Ala Ala Gly
50                  55                  60

Ala Gly Thr Gly Gly Ala Gly Pro Ala Gly Arg Leu Leu Pro Pro Pro
65                  70                  75                  80

Ala Pro Gly Ser Pro Ala Ala Pro Ala Ala Val Ser Pro Ala Ala Gly
                85                  90                  95

Gln Pro Arg Pro Pro Ala Pro Ala Ser Arg Gly Pro Met Pro Ala Arg
                100                 105                 110

Ile Gly Tyr Tyr Glu Ile Asp Arg Thr Ile Gly Lys Gly Asn Phe Ala
                115                 120                 125

Val Val Lys Arg Ala Thr His Leu Val Thr Lys Ala Lys Val Ala Ile
                130                 135                 140

Lys Ile Ile Asp Lys Thr Gln Leu Asp Glu Glu Asn Leu Lys Lys Ile
145                 150                 155                 160

Phe Arg Glu Val Gln Ile Met Lys Met Leu Cys His Pro His Ile Ile
                165                 170                 175

Arg Leu Tyr Gln Val Met Glu Thr Glu Arg Met Ile Tyr Leu Val Thr
                180                 185                 190

Glu Tyr Ala Ser Gly Gly Glu Ile Phe Asp His Leu Val Ala His Gly
                195                 200                 205

Arg Met Ala Glu Lys Glu Ala Arg Arg Lys Phe Lys Gln Ile Val Thr
                210                 215                 220

Ala Val Tyr Phe Cys His Cys Arg Asn Ile Val His Arg Asp Leu Lys
225                 230                 235                 240

Ala Glu Asn Leu Leu Leu Asp Ala Asn Leu Asn Ile Lys Ile Ala Asp
                245                 250                 255

Phe Gly Phe Ser Asn Leu Phe Thr Pro Gly Gln Leu Leu Lys Thr Trp
                260                 265                 270

Cys Gly Ser Pro Pro Tyr Ala Ala Pro Glu Leu Phe Glu Gly Lys Glu
                275                 280                 285

Tyr Asp Gly Pro Lys Val Asp Ile Trp Ser Leu Gly Val Val Leu Tyr
```

```
            290                 295                 300
Val Leu Val Cys Gly Ala Leu Pro Phe Asp Gly Ser Thr Leu Gln Asn
305                 310                 315                 320

Leu Arg Ala Arg Val Leu Ser Gly Lys Phe Arg Ile Pro Phe Phe Met
                325                 330                 335

Ser Thr Glu Cys Glu His Leu Ile Arg His Met Leu Val Leu Asp Pro
                340                 345                 350

Asn Lys Arg Leu Ser Met Glu Gln Ile Cys Lys His Lys Trp Met Lys
                355                 360                 365

Leu Gly Asp Ala Asp Pro Asn Phe Asp Arg Leu Ile Ala Glu Cys Gln
370                 375                 380

Gln Leu Lys Glu Glu Arg Gln Val Asp Pro Leu Asn Glu Asp Val Leu
385                 390                 395                 400

Leu Ala Met Glu Asp Met Gly Leu Asp Lys Glu Gln Thr Leu Gln Ser
                405                 410                 415

Leu Arg Ser Asp Ala Tyr Asp His Tyr Ser Ala Ile Tyr Ser Leu Leu
                420                 425                 430

Cys Asp Arg His Lys Arg His Lys Thr Leu Arg Leu Gly Ala Leu Pro
                435                 440                 445

Ser Met Pro Arg Ala Leu Ala Phe Gln Ala Pro Val Asn Ile Gln Ala
450                 455                 460

Glu Gln Ala Gly Thr Ala Met Asn Ile Ser Val Pro Gln Val Gln Leu
465                 470                 475                 480

Ile Asn Pro Glu Asn Gln Ile Val Glu Pro Asp Gly Thr Leu Asn Leu
                485                 490                 495

Asp Ser Asp Glu Gly Glu Glu Pro Ser Pro Glu Ala Leu Val Arg Tyr
                500                 505                 510

Leu Ser Met Arg Arg His Thr Val Gly Val Ala Asp Pro Arg Thr Glu
                515                 520                 525

Val Met Glu Asp Leu Gln Lys Leu Leu Pro Gly Phe Pro Gly Val Asn
                530                 535                 540

Pro Gln Ala Pro Phe Leu Gln Val Ala Pro Asn Val Asn Phe Met His
545                 550                 555                 560

Asn Leu Leu Pro Met Gln Asn Leu Gln Pro Thr Gly Gln Leu Glu Tyr
                565                 570                 575

Lys Glu Gln Ser Leu Leu Gln Pro Pro Thr Leu Gln Leu Leu Asn Gly
                580                 585                 590

Met Gly Pro Leu Gly Arg Arg Ala Ser Asp Gly Gly Ala Asn Ile Gln
                595                 600                 605

Leu His Ala Gln Gln Leu Leu Lys Arg Pro Arg Gly Pro Ser Pro Leu
610                 615                 620

Val Thr Met Thr Pro Ala Val Pro Ala Val Thr Pro Val Asp Glu Glu
625                 630                 635                 640

Ser Ser Asp Gly Glu Pro Asp Gln Glu Ala Val Gln Ser Ser Thr Tyr
                645                 650                 655

Lys Asp Ser Asn Thr Leu His Leu Pro Thr Glu Arg Phe Ser Pro Val
                660                 665                 670

Arg Arg Phe Ser Asp Gly Ala Ala Ser Ile Gln Ala Phe Lys Ala His
                675                 680                 685

Leu Glu Lys Met Gly Asn Asn Ser Ser Ile Lys Gln Leu Gln Gln Glu
                690                 695                 700

Cys Glu Gln Leu Gln Lys Met Tyr Gly Gly Gln Ile Asp Glu Arg Thr
705                 710                 715                 720
```

```
Leu Glu Lys Thr Gln Gln Gln His Met Leu Tyr Gln Glu Gln His
            725                 730                 735

His Gln Ile Leu Gln Gln Ile Gln Asp Ser Ile Cys Pro Pro Gln
            740                 745                 750

Pro Ser Pro Pro Leu Gln Ala Ala Cys Glu Asn Gln Pro Ala Leu Leu
            755                 760                 765

Thr His Gln Leu Gln Arg Leu Arg Ile Gln Pro Ser Ser Pro Pro Pro
        770                 775                 780

Asn His Pro Asn Asn His Leu Phe Arg Gln Pro Ser Asn Ser Pro Pro
785                 790                 795                 800

Pro Met Ser Ser Ala Met Ile Gln Pro His Gly Ala Ala Ser Ser Ser
                805                 810                 815

Gln Phe Gln Gly Leu Pro Ser Arg Ser Ala Ile Phe Gln Gln Pro
            820                 825                 830

Glu Asn Cys Ser Ser Pro Pro Asn Val Ala Leu Thr Cys Leu Gly Met
                835                 840                 845

Gln Gln Pro Ala Gln Ser Gln Gln Val Thr Ile Gln Val Gln Glu Pro
        850                 855                 860

Val Asp Met Leu Ser Asn Met Pro Gly Thr Ala Gly Ser Ser Gly
865                 870                 875                 880

Arg Gly Ile Ser Ile Ser Pro Ala Gly Gln Met Gln Met Gln His
                885                 890                 895

Arg Thr Asn Leu Met Ala Thr Leu Ser Tyr Gly His Arg Pro Leu Ser
                900                 905                 910

Lys Gln Leu Ser Ala Asp Ser Ala Glu Ala His Ser Leu Asn Val Asn
        915                 920                 925

Arg Phe Ser Pro Ala Asn Tyr Asp Gln Ala His Leu His Pro His Leu
        930                 935                 940

Phe Ser Asp Gln Ser Arg Gly Ser Pro Ser Ser Tyr Ser Pro Ser Thr
945                 950                 955                 960

Gly Val Gly Phe Ser Pro Thr Gln Ala Leu Lys Val Pro Pro Leu Asp
                965                 970                 975

Gln Phe Pro Thr Phe Pro Pro Ser Ala His Gln Gln Pro Pro His Tyr
            980                 985                 990

Thr Thr Ser Ala Leu Gln Gln Ala Leu Leu Ser Pro Thr Pro Pro Asp
        995                1000                1005

Tyr Thr Arg His Gln Gln Val Pro His Ile Leu Gln Gly Leu Leu
       1010                1015                1020

Ser Pro Arg His Ser Leu Thr Gly His Ser Asp Ile Arg Leu Pro
       1025                1030                1035

Pro Thr Glu Phe Ala Gln Leu Ile Lys Arg Gln Gln Gln Gln Arg
       1040                1045                1050

Gln Gln Gln Gln Gln Gln Gln Gln Gln Glu Tyr Gln Glu Leu
       1055                1060                1065

Phe Arg His Met Asn Gln Gly Asp Ala Gly Ser Leu Ala Pro Ser
       1070                1075                1080

Leu Gly Gly Gln Ser Met Thr Glu Arg Gln Ala Leu Ser Tyr Gln
       1085                1090                1095

Asn Ala Asp Ser Tyr His His Thr Ser Pro Gln His Leu Leu
       1100                1105                1110

Gln Ile Arg Ala Gln Glu Cys Val Ser Gln Ala Ser Ser Pro Thr
       1115                1120                1125

Pro Pro His Gly Tyr Ala His Gln Pro Ala Leu Met His Ser Glu
       1130                1135                1140
```

```
Ser Met Glu Glu Asp Cys Ser Cys Glu Gly Ala Lys Asp Gly Phe
    1145                1150                1155

Gln Asp Ser Lys Ser Ser Ser Thr Leu Thr Lys Gly Cys His Asp
    1160                1165                1170

Ser Pro Leu Leu Leu Ser Thr Gly Gly Pro Gly Asp Pro Glu Ser
    1175                1180                1185

Leu Leu Gly Thr Val Ser His Ala Gln Glu Leu Gly Ile His Pro
    1190                1195                1200

Tyr Gly His Gln Pro Thr Ala Ala Phe Ser Lys Asn Lys Val Pro
    1205                1210                1215

Ser Arg Glu Pro Val Ile Gly Asn Cys Met Asp Arg Ser Ser Pro
    1220                1225                1230

Gly Gln Ala Val Glu Leu Pro Asp His Asn Gly Leu Gly Tyr Pro
    1235                1240                1245

Ala Arg Pro Ser Val His Glu His His Arg Pro Arg Ala Leu Gln
    1250                1255                1260

Arg His His Thr Ile Gln Asn Ser Asp Asp Ala Tyr Val Gln Leu
    1265                1270                1275

Asp Asn Leu Pro Gly Met Ser Leu Val Ala Gly Lys Ala Leu Ser
    1280                1285                1290

Ser Ala Arg Met Ser Asp Ala Val Leu Ser Gln Ser Ser Leu Met
    1295                1300                1305

Gly Ser Gln Gln Phe Gln Asp Gly Glu Asn Glu Glu Cys Gly Ala
    1310                1315                1320

Ser Leu Gly Gly His Glu His Pro Asp Leu Ser Asp Gly Ser Gln
    1325                1330                1335

His Leu Asn Ser Ser Cys Tyr Pro Ser Thr Cys Ile Thr Asp Ile
    1340                1345                1350

Leu Leu Ser Tyr Lys His Pro Glu Val Ser Phe Ser Met Glu Gln
    1355                1360                1365

Ala Gly Val
    1370

<210> SEQ ID NO 17
<211> LENGTH: 926
<212> TYPE: PRT
<213> ORGANISM: Homo sapiens

<400> SEQUENCE: 17

Met Val Met Ala Asp Gly Pro Arg His Leu Gln Arg Gly Pro Val Arg
1               5                   10                  15

Val Gly Phe Tyr Asp Ile Glu Gly Thr Leu Gly Lys Gly Asn Phe Ala
            20                  25                  30

Val Val Lys Leu Gly Arg His Arg Ile Thr Lys Thr Glu Val Ala Ile
        35                  40                  45

Lys Ile Ile Asp Lys Ser Gln Leu Asp Ala Val Asn Leu Glu Lys Ile
    50                  55                  60

Tyr Arg Glu Val Gln Ile Met Lys Met Leu Asp His Pro His Ile Ile
65                  70                  75                  80

Lys Leu Tyr Gln Val Met Glu Thr Lys Ser Met Leu Tyr Leu Val Thr
                85                  90                  95

Glu Tyr Ala Lys Asn Gly Glu Ile Phe Asp Tyr Leu Ala Asn His Gly
            100                 105                 110

Arg Leu Asn Glu Ser Glu Ala Arg Arg Lys Phe Trp Gln Ile Leu Ser
        115                 120                 125
```

```
Ala Val Asp Tyr Cys His Gly Arg Lys Ile Val His Arg Asp Leu Lys
    130                 135                 140
Ala Glu Asn Leu Leu Leu Asp Asn Asn Met Asn Ile Lys Ile Ala Asp
145                 150                 155                 160
Phe Gly Phe Gly Asn Phe Phe Lys Ser Gly Glu Leu Leu Ala Thr Trp
                165                 170                 175
Cys Gly Ser Pro Pro Tyr Ala Ala Pro Glu Val Phe Glu Gly Gln Gln
            180                 185                 190
Tyr Glu Gly Pro Gln Leu Asp Ile Trp Ser Met Gly Val Val Leu Tyr
        195                 200                 205
Val Leu Val Cys Gly Ala Leu Pro Phe Asp Gly Pro Thr Leu Pro Ile
    210                 215                 220
Leu Arg Gln Arg Val Leu Glu Gly Arg Phe Arg Ile Pro Tyr Phe Met
225                 230                 235                 240
Ser Glu Asp Cys Glu His Leu Ile Arg Arg Met Leu Val Leu Asp Pro
                245                 250                 255
Ser Lys Arg Leu Thr Ile Ala Gln Ile Lys Glu His Lys Trp Met Leu
                260                 265                 270
Ile Glu Val Pro Val Gln Arg Pro Val Leu Tyr Pro Gln Glu Gln Glu
            275                 280                 285
Asn Glu Pro Ser Ile Gly Glu Phe Asn Glu Gln Val Leu Arg Leu Met
290                 295                 300
His Ser Leu Gly Ile Asp Gln Gln Lys Thr Ile Glu Ser Leu Gln Asn
305                 310                 315                 320
Lys Ser Tyr Asn His Phe Ala Ala Ile Tyr Phe Leu Leu Val Glu Arg
                325                 330                 335
Leu Lys Ser His Arg Ser Ser Phe Pro Val Gln Arg Leu Asp Gly
                340                 345                 350
Arg Gln Arg Arg Pro Ser Thr Ile Ala Glu Gln Thr Val Ala Lys Ala
                355                 360                 365
Gln Thr Val Gly Leu Pro Val Thr Met His Ser Pro Asn Met Arg Leu
    370                 375                 380
Leu Arg Ser Ala Leu Leu Pro Gln Ala Ser Asn Val Glu Ala Phe Ser
385                 390                 395                 400
Phe Pro Ala Ser Gly Cys Gln Ala Glu Ala Phe Met Glu Glu
                405                 410                 415
Cys Val Asp Thr Pro Lys Val Asn Gly Cys Leu Leu Asp Pro Val Pro
                420                 425                 430
Pro Val Leu Val Arg Lys Gly Cys Gln Ser Leu Pro Ser Asn Met Met
            435                 440                 445
Glu Thr Ser Ile Asp Glu Gly Leu Glu Thr Gly Glu Ala Glu Glu
        450                 455                 460
Asp Pro Ala His Ala Phe Glu Ala Phe Gln Ser Thr Arg Ser Gly Gln
465                 470                 475                 480
Arg Arg His Thr Leu Ser Glu Val Thr Asn Gln Leu Val Met Pro
                485                 490                 495
Gly Ala Gly Lys Ile Phe Ser Met Asn Asp Ser Pro Ser Leu Asp Ser
            500                 505                 510
Val Asp Ser Glu Tyr Asp Met Gly Ser Val Arg Asp Leu Asn Phe
        515                 520                 525
Leu Glu Asp Asn Pro Ser Leu Lys Asp Ile Met Leu Ala Asn Gln Pro
    530                 535                 540
Ser Pro Arg Met Thr Ser Pro Phe Ile Ser Leu Arg Pro Thr Asn Pro
```

```
                545                 550                 555                 560
Ala Met Gln Ala Leu Ser Ser Gln Lys Arg Glu Val His Asn Arg Ser
            565                 570                 575

Pro Val Ser Phe Arg Glu Gly Arg Ala Ser Asp Thr Ser Leu Thr
        580                 585                 590

Gln Gly Ile Val Ala Phe Arg Gln His Leu Gln Asn Leu Ala Arg Thr
        595                 600                 605

Lys Gly Ile Leu Glu Leu Asn Lys Val Gln Leu Leu Tyr Glu Gln Ile
    610                 615                 620

Gly Pro Glu Ala Asp Pro Asn Leu Ala Pro Ala Pro Gln Leu Gln
625                 630                 635                 640

Asp Leu Ala Ser Ser Cys Pro Gln Glu Val Ser Gln Gln Glu
                645                 650                 655

Ser Val Ser Thr Leu Pro Ala Ser Val His Pro Gln Leu Ser Pro Arg
            660                 665                 670

Gln Ser Leu Glu Thr Gln Tyr Leu Gln His Arg Leu Gln Lys Pro Ser
        675                 680                 685

Leu Leu Ser Lys Ala Gln Asn Thr Cys Gln Leu Tyr Cys Lys Glu Pro
    690                 695                 700

Pro Arg Ser Leu Glu Gln Gln Leu Glu His Arg Leu Gln Gln Lys
705                 710                 715                 720

Arg Leu Phe Leu Gln Lys Ser Gln Leu Gln Ala Tyr Phe Asn Gln
                725                 730                 735

Met Gln Ile Ala Glu Ser Ser Tyr Pro Gln Pro Ser Gln Gln Leu Pro
            740                 745                 750

Leu Pro Arg Gln Glu Thr Pro Pro Ser Gln Gln Ala Pro Pro Phe
        755                 760                 765

Ser Leu Thr Gln Pro Leu Ser Pro Val Leu Glu Pro Ser Ser Glu Gln
770                 775                 780

Met Gln Tyr Ser Pro Phe Leu Ser Gln Tyr Gln Glu Met Gln Leu Gln
785                 790                 795                 800

Pro Leu Pro Ser Thr Ser Gly Pro Arg Ala Ala Pro Leu Pro Thr
                805                 810                 815

Gln Leu Gln Gln Gln Pro Pro Pro Pro Pro Pro Pro Pro
            820                 825                 830

Arg Gln Pro Gly Ala Ala Pro Ala Pro Leu Gln Phe Ser Tyr Gln Thr
        835                 840                 845

Cys Glu Leu Pro Ser Ala Ala Ser Pro Ala Pro Asp Tyr Pro Thr Pro
    850                 855                 860

Cys Gln Tyr Pro Val Asp Gly Ala Gln Gln Ser Asp Leu Thr Gly Pro
865                 870                 875                 880

Asp Cys Pro Arg Ser Pro Gly Leu Gln Glu Ala Pro Ser Ser Tyr Asp
                885                 890                 895

Pro Leu Ala Leu Ser Glu Leu Pro Gly Leu Phe Asp Cys Glu Met Leu
            900                 905                 910

Asp Ala Val Asp Pro Gln His Asn Gly Tyr Val Leu Val Asn
        915                 920                 925

<210> SEQ ID NO 18
<211> LENGTH: 926
<212> TYPE: PRT
<213> ORGANISM: Homo sapiens

<400> SEQUENCE: 18

Met Val Met Ala Asp Gly Pro Arg His Leu Gln Arg Gly Pro Val Arg
```

```
              1               5                  10                 15
Val Gly Phe Tyr Asp Ile Glu Gly Thr Leu Gly Lys Gly Asn Phe Ala
                    20                 25                 30

Val Val Lys Leu Gly Arg His Arg Ile Thr Lys Thr Glu Val Ala Ile
            35                 40                 45

Lys Ile Ile Asp Lys Ser Gln Leu Asp Ala Val Asn Leu Glu Lys Ile
    50                 55                 60

Tyr Arg Glu Val Gln Ile Met Lys Met Leu Asp His Pro His Ile Ile
65                     70                 75                 80

Lys Leu Tyr Gln Val Met Glu Thr Lys Ser Met Leu Tyr Leu Val Thr
                85                 90                 95

Glu Tyr Ala Lys Asn Gly Glu Ile Phe Asp Tyr Leu Ala Asn His Gly
                100                105                110

Arg Leu Asn Glu Ser Glu Ala Arg Arg Lys Phe Trp Gln Ile Leu Ser
            115                120                125

Ala Val Asp Tyr Cys His Gly Arg Lys Ile Val His Arg Asp Leu Lys
    130                135                140

Ala Glu Asn Leu Leu Leu Asp Asn Asn Met Asn Ile Lys Ile Ala Asp
145                150                155                160

Phe Gly Phe Gly Asn Phe Phe Lys Ser Gly Glu Leu Leu Ala Thr Trp
                165                170                175

Cys Gly Ser Pro Pro Tyr Ala Ala Pro Glu Val Phe Glu Gly Gln Gln
                180                185                190

Tyr Glu Gly Pro Gln Leu Asp Ile Trp Ser Met Gly Val Val Leu Tyr
                195                200                205

Val Leu Val Cys Gly Ala Leu Pro Phe Asp Gly Pro Thr Leu Pro Ile
    210                215                220

Leu Arg Gln Arg Val Leu Glu Gly Arg Phe Arg Ile Pro Tyr Phe Met
225                230                235                240

Ser Glu Asp Cys Glu His Leu Ile Arg Arg Met Leu Val Leu Asp Pro
            245                250                255

Ser Lys Arg Leu Thr Ile Ala Gln Ile Lys Glu His Lys Trp Met Leu
            260                265                270

Ile Glu Val Pro Val Gln Arg Pro Val Leu Tyr Pro Gln Glu Gln Glu
    275                280                285

Asn Glu Pro Ser Ile Gly Glu Phe Asn Glu Gln Val Leu Arg Leu Met
            290                295                300

His Ser Leu Gly Ile Asp Gln Gln Lys Thr Ile Glu Ser Leu Gln Asn
305                310                315                320

Lys Ser Tyr Asn His Phe Ala Ala Ile Tyr Phe Leu Leu Val Glu Arg
                325                330                335

Leu Lys Ser His Arg Ser Ser Phe Pro Val Glu Gln Arg Leu Asp Gly
            340                345                350

Arg Gln Arg Arg Pro Ser Thr Ile Ala Glu Gln Thr Val Ala Lys Ala
            355                360                365

Gln Thr Val Gly Leu Pro Val Thr Met His Ser Pro Asn Met Arg Leu
    370                375                380

Leu Arg Ser Ala Leu Leu Pro Gln Ala Ser Asn Val Glu Ala Phe Ser
385                390                395                400

Phe Pro Ala Ser Gly Cys Gln Ala Glu Ala Phe Met Glu Glu Glu
                405                410                415

Cys Val Asp Thr Pro Lys Val Asn Gly Cys Leu Leu Asp Pro Val Pro
            420                425                430
```

-continued

Pro Val Leu Val Arg Lys Gly Cys Gln Ser Leu Pro Ser Asn Met Met
    435                 440                 445

Glu Thr Ser Ile Asp Glu Gly Leu Glu Thr Glu Gly Glu Ala Glu Glu
450                 455                 460

Asp Pro Ala His Ala Phe Glu Ala Phe Gln Ser Thr Arg Ser Gly Gln
465                 470                 475                 480

Arg Arg His Thr Leu Ser Glu Val Thr Asn Gln Leu Val Val Met Pro
                485                 490                 495

Gly Ala Gly Lys Ile Phe Ser Met Asn Asp Ser Pro Ser Leu Asp Ser
            500                 505                 510

Val Asp Ser Glu Tyr Asp Met Gly Ser Val Gln Arg Asp Leu Asn Phe
        515                 520                 525

Leu Glu Asp Asn Pro Ser Leu Lys Asp Ile Met Leu Ala Asn Gln Pro
    530                 535                 540

Ser Pro Arg Met Thr Ser Pro Phe Ile Ser Leu Arg Pro Thr Asn Pro
545                 550                 555                 560

Ala Met Gln Ala Leu Ser Ser Gln Lys Arg Glu Val His Asn Arg Ser
                565                 570                 575

Pro Val Ser Phe Arg Glu Gly Arg Arg Ala Ser Asp Thr Ser Leu Thr
            580                 585                 590

Gln Gly Ile Val Ala Phe Arg Gln His Leu Gln Asn Leu Ala Arg Thr
        595                 600                 605

Lys Gly Ile Leu Glu Leu Asn Lys Val Gln Leu Leu Tyr Glu Gln Ile
    610                 615                 620

Gly Pro Glu Ala Asp Pro Asn Leu Ala Pro Ala Ala Pro Gln Leu Gln
625                 630                 635                 640

Asp Leu Ala Ser Ser Cys Pro Gln Glu Glu Val Ser Gln Gln Gln Glu
                645                 650                 655

Ser Val Ser Thr Leu Pro Ala Ser Val His Pro Gln Leu Ser Pro Arg
            660                 665                 670

Gln Ser Leu Glu Thr Gln Tyr Leu Gln His Arg Leu Gln Lys Pro Ser
        675                 680                 685

Leu Leu Ser Lys Ala Gln Asn Thr Cys Gln Leu Tyr Cys Lys Glu Pro
    690                 695                 700

Pro Arg Ser Leu Glu Gln Gln Leu Gln Glu His Arg Leu Gln Gln Lys
705                 710                 715                 720

Arg Leu Phe Leu Gln Lys Gln Ser Gln Leu Gln Ala Tyr Phe Asn Gln
                725                 730                 735

Met Gln Ile Ala Glu Ser Ser Tyr Pro Gln Pro Ser Gln Gln Leu Pro
            740                 745                 750

Leu Pro Arg Gln Glu Thr Pro Pro Ser Gln Ala Pro Pro Phe
        755                 760                 765

Ser Leu Thr Gln Pro Leu Ser Pro Val Leu Glu Pro Ser Ser Glu Gln
    770                 775                 780

Met Gln Tyr Ser Pro Phe Leu Ser Gln Tyr Gln Glu Met Gln Leu Gln
785                 790                 795                 800

Pro Leu Pro Ser Thr Ser Gly Pro Arg Ala Ala Pro Leu Pro Thr
                805                 810                 815

Gln Leu Gln Gln Gln Pro Pro Pro Pro Pro Pro Pro Pro
            820                 825                 830

Arg Gln Pro Gly Ala Ala Pro Ala Pro Leu Gln Phe Ser Tyr Gln Thr
        835                 840                 845

Cys Glu Leu Pro Ser Ala Ala Ser Pro Ala Pro Asp Tyr Pro Thr Pro
    850                 855                 860

```
Cys Gln Tyr Pro Val Asp Gly Ala Gln Ser Asp Leu Thr Gly Pro
865                 870                 875                 880

Asp Cys Pro Arg Ser Pro Gly Leu Gln Glu Ala Pro Ser Ser Tyr Asp
                885                 890                 895

Pro Leu Ala Leu Ser Glu Leu Pro Gly Leu Phe Asp Cys Glu Met Leu
            900                 905                 910

Asp Ala Val Asp Pro Gln His Asn Gly Tyr Val Leu Val Asn
            915                 920                 925
```

MARKS AS MODIFERS OF THE PTEN PATHWAY AND METHODS OF USE

REFERENCE TO RELATED APPLICATIONS

This application claims priority to U.S. provisional patent application 60/479,768 filed Jun. 19, 2003. The contents of the prior application are hereby incorporated in their entirety.

BACKGROUND OF THE INVENTION

The AKT signaling pathway is frequently hyperactivated by a variety of mechanisms in a wide range of human cancers, including melanoma, breast, lung, prostate, and ovarian tumors (see Vivanco I and Sawyers C L (2002) Nat Rev Cancer. 2(7):489-501; Scheid M P and Woodgett J R (2001) J Mammary Gland Biol Neoplasia. 6(1):83-99). In tumor cells, the AKT protein kinase activity can be elevated by amplification and overexpression of the AKT2 gene, or by increased production of phosphatidylinositol (3, 4, 5) trisphosphate ($PIP_3$), which activates AKT by recruitment to the plasma membrane. In normal phosphoinositide metabolism, phosphatidylinositol (3, 4) bisphosphate ($PIP_2$) is phosphorylated by phosphatidylinositol 3-kinase (PI3K) to generate $PIP_3$, and $PIP_3$ is dephosphorylated back to $PIP_2$ by the lipid phosphatase PTEN. $PIP_3$ levels in tumors can be enhanced by amplification and overexpression of PI3K, or by hyperactivation of the PI3K activator IGF receptor. Most commonly, however, $PIP_3$ levels in tumor cells are elevated by mutation or deletion of the PTEN tumor suppressor, at rates as high as 40-50% of prostate cancers. The AKT pathway promotes tumor progression by enhancing cell proliferation, growth, survival, and motility, and by suppressing apoptosis. These effects are mediated by several AKT substrates, including the related transcription factors FKHR and AFX, for which phosphorylation by AKT mediates nuclear export.

All of the major AKT pathway components have structural and functional orthologs in *C. elegans* that function in dauer larva formation (see Wolkow C A et al. (2002) J Biol Chem 277(51):49591-7; Paradis S et al (1999) Genes Dev. 13(11): 1438-52). Normally, environmental cues of low food (bacteria) levels, high dauer pheromone concentration, and high temperature trigger a developmental decision that signals alternative differentiation pathways in all tissues and entry into a diapause (dauer) arrest. Inactivating mutations or RNAi of the AKT orthologs akt-1 and akt-2, or the PI3K ortholog age-1, or the IGP receptor daf-2, produce a dauer-constitutive (Daf-c) phenotype; in which animals form dauers even under environmental conditions that normally induce development to adulthood. Conversely, inactivating mutations in the PTEN ortholog daf-18, or the FKHR and AFX ortholog daf-16, generate a dauer-defective (Daf-d) phenotype and prevent dauer formation regardless of environmental conditions. A daf-18 deletion mutant fully suppresses the Daf-c phenotype of age-1 and daf-2 mutations (Gil E B et al (1999) Proc Natl Acad Sci USA. 96(6):2925-30; Mihaylova V T et al (1999) Proc Natl Acad Sci USA. 96(13):7427-32), and we have identified two loss-of-function mutations that allow non-dauer development of the heat-sensitive daf-2 (1370) allele at the non-permissive temperature of 25° C. daf-18 (ep496) is a nonsense mutation at amino acid E455, and daf-18 (ep497) is a missense mutation predicted to cause the amino acid substitution G80D. The Daf-d phenotype of double mutants daf-18 (ep496); daf-2 (e1370) and daf-18 (ep497); and daf-2 (e1370) can be reverted to a Daf-c phenotype by RNAi of akt-1 or age-1, indicating that the double mutants display increased AKT signaling.

Microtubules have a central role in the regulation cell shape and polarity during differentiation, chromosome partitioning at mitosis, and intracellular transport. Microtubules undergo rearrangements involving rapid transitions between stable and dynamic states during these processes. Microtubule affinity regulating kinases (MARK) are a novel family of protein kinases that phosphorylate microtubule-associated proteins and trigger microtubule disruption (Drewes, G., et al. (1997) Cell 89: 297-308). Mammalian SNF1 like kinase (SNF1LK) is a serine/threonine kinase similar to Snf1 protein kinase, of *S. cerevisiae*, which is involved in the response to nutritional stress.

The ability to manipulate the genomes of model organisms such as *C. elegans* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Dulubova I, et al, J Neurochem April 2001; 77(1):229-38; Cai T, et al., Diabetolbgia January 2001; 44(1):81-8; Pasquinelli A E, et al., Nature. Nov. 2, 2000; 408(6808):37-8; Ivanov I P, et al., EMBO J Apr. 17, 2000; 19(8): 1907-17; Vajo Z et al., Mamm Genome October 1999; 10(10):1000-4). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as PTEN, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the PTEN pathway in *C. elegans*, and identified their human orthologs, hereinafter referred to as Microtubule affinity-regulating kinases (MARK). The invention provides methods for utilizing these PTEN modifier genes and polypeptides to identify MARK-modulating agents that are candidate therapeutic agents that can be used in the treatment of disorders associated with defective or impaired PTEN function and/or MARK function. Preferred MARK-modulating agents specifically bind to MARK polypeptides and restore PTEN function. Other preferred MARK-modulating agents are nucleic acid modulators such as antisense oligomers and RNAi that repress MARK gene expression or product activity by, for example, binding to and inhibiting the respective nucleic acid (i.e. DNA or mRNA).

MARK modulating agents may be evaluated by any convenient in vitro or in vivo assay for molecular interaction with a MARK polypeptide or nucleic acid. In one embodiment, candidate MARK modulating agents are tested with an assay system comprising a MARK polypeptide or nucleic acid. Agents that produce a change in the activity of the assay system relative to controls are identified as candidate PTEN modulating agents. The assay system may be cell-based or cell-free. MARK-modulating agents include MARK related proteins (e.g. dominant negative mutants, and biotherapeutics); MARK-specific antibodies; MARK-specific antisense oligomers and other nucleic acid modulators; and chemical agents that specifically bind to or interact with MARK or compete with MARK binding partner (e.g. by binding to a MARK binding partner). In one specific embodiment, a small molecule modulator is identified using a kinase assay. In specific-embodiments, the screening assay system is selected from a binding assay, an apoptosis assay, a cell proliferation assay, an angiogenesis assay, and a hypoxic induction assay.

In another embodiment, candidate-PTEN pathway modulating agents are further tested using a second assay system that detects changes in the PTEN pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the PTEN pathway, such as an angiogenic, apoptotic, or cell proliferation disorder (e.g. cancer).

The invention further provides methods for modulating the MARK function and/or the PTEN pathway in a mammalian cell by contacting the mammalian cell with an agent that specifically binds a MARK polypeptide or nucleic acid. The agent may be a small molecule modulator, a nucleic acid modulator, or an antibody and may be administered to a mammalian animal predetermined to have a pathology associated with the PTEN pathway.

DETAILED DESCRIPTION OF THE INVENTION

We designed a genetic screen to identify suppressor genes that, when inactivated, decrease signaling through the AKT pathway. The function of individual genes was inactivated by RNAi in the daf-18 (ep496); daf-2 (e1370) double mutant by soaking L1 larvae in double-stranded RNA for each gene. Methods for using RNAi to silence genes in *C. elegans* are known in the art (Fire A, et al., 1998 Nature 391:806-811; Fire, A. Trends Genet. 15, 358-363 (1999); WO9932619). Genes causing altered phenotypes in the worms were identified as modifiers of the PTEN pathway. The PAR-1 gene was identified as a modifier of the PTEN pathway. Accordingly, vertebrate orthologs of these modifiers, and preferably the human orthologs, MARK genes (i.e., nucleic acids and polypeptides) are attractive drug targets for the treatment of pathologies associated with a defective PTEN signaling pathway, such as cancer.

In vitro and in vivo methods of assessing MARK function are provided herein. Modulation of the MARK or their respective binding partners is useful for understanding the association of the PTEN pathway and its members in normal and disease conditions and for developing diagnostics and therapeutic modalities for PTEN related pathologies. MARK-modulating agents that act by inhibiting or enhancing MARK expression, directly or indirectly, for example, by affecting a MARK function such as enzymatic (e.g., catalytic) or binding activity, can be identified using methods provided herein. MARK modulating agents are useful in diagnosis, therapy and pharmaceutical development.

Nucleic Acids and Polypeptides of the Invention

Sequences related to MARK nucleic acids and polypeptides that can be used in the invention are disclosed in Genbank (referenced by Genbank identifier (GI) number) as GI#s 17382968 (SEQ ID NO:1), 27597093 (SEQ ID NO:5), 23620491 (SEQ ID NO:6), 39812204 (SEQ ID NO:7), 13386467 (SEQ ID NO:8), 14133228 (SEQ ID NO:9), 30156409 (SEQ ID NO: 10), 22064826 (SEQ ID NO:11), 30314571 (SEQ ID NO:12), and 38569459 (SEQ ID NO:13), for nucleic acid, and GI#s 9978891 (SEQ D NO:14), 27597094 (SEQ ID NO:15), 14133229 (SEQ ID NO:16), 14770402 (SEQ ID NO:17), and 38569460 (SEQ ID NO: 18) for polypeptide sequences. Additionally, nucleic acid sequences of SEQ ID NOs:2, 3, and 4 can also be used in the invention.

The term "MARK polypeptide" refers to a full-length MARK protein or a functionally active fragment or derivative thereof A "functionally active" MARK fragment or derivative exhibits one or more functional activities associated with a full-length, wild-type MARK protein, such as antigenic or immunogenic activity, enzymatic activity, ability to bind natural cellular substrates, etc. The functional activity of MARK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active MARK polypeptide is a MARK derivative capable of rescuing defective endogenous MARK activity, such as in cell based or animal assays; the rescuing derivative may be from the same or a different species. For purposes herein, functionally active fragments also include those fragments that comprise one or more structural domains of a MARK, such as a kinase domain or a binding domain. Protein domains can be identified using the PFAM program (Bateman A., et al., Nucleic Acids Res, 1999, 27:260-2). For example, the kinase domain (PFAM 00069) of MARK from GI#s 27597094, 14133229, and 38569460 (SEQ ID NOs:15, 16, and 18, respectively) is located respectively at approximately amino acid residues 27 to 278, 116 to 367, and 20 to 271. Methods for obtaining MARK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a MARK. In further preferred embodiments, the fragment comprises the entire functionally active domain.

The term "MARK nucleic acid" refers to a DNA or RNA molecule that encodes a MARK polypeptide. Preferably, the MARK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human MARK. Methods of identifying orthologs are known in the art. Normally, orthologs in different species, retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P. Proc Natl Acad Sci (1998) 95:5849-5856; Huynen M A et al., Genome Research (2000) 10: 1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a MARK. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10; John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a MARK under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MARK Nucleic Acids and Polypeptides MARK nucleic acids and polypeptides are useful for identifying and testing agents that modulate MARK function and for other applications related to the involvement of MARK in the PTEN pathway. MARK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MARK protein for assays used to assess MARK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, 2 edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MARK, is expressed in a cell line known to have defective PTEN function. The recombinant cells are used in cell-based screening assay systems of the invention, as described further below.

The nucleotide sequence encoding a MARK polypeptide can be inserted into any appropriate expression vector. The necessary transcriptional and translational signals, including promoter/enhancer element, can derive from the native MARK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or, specifically processes the gene product may be used.

To detect expression of the MARK gene product, the expression vector can comprise a promoter operably linked to a MARK gene nucleic acid, one or more origins of replication, and, one or more selectable markers (e.g. thymidine kinase activity, resistance to antibiotics, etc.). Alternatively, recombinant expression vectors can be identified by assaying for the expression of the MARK gene product based on the physical or functional properties of the MARK protein in in vitro assay systems (e.g. immunoassays).

The MARK protein, fragment, or derivative may be optionally expressed as a fusion, or chimeric protein product (i.e. it is joined via a peptide bond to a heterologous protein sequence of a different protein), for example to facilitate purification of detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MARK gene sequence is identified, the gene product can be isolated and purified using standard methods (e.g. ion exchange, affinity, and gel exclusion chromatography; centrifugation; differential solubility; electrophoresis). Alternatively, native MARK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MARK or other genes associated with the PTEN pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MARK expression may be used in in vivo assays to, test for activity of a candidate PTEN modulating agent, or to further assess the role of MARK in a PTEN pathway process such as apoptosis or cell proliferation. Preferably, the altered MARK expression results in a detectable phenotype, such as decreased or increased levels of cell proliferation, angiogenesis, or apoptosis compared to control animals having normal MARK expression. The genetically modified animal may additionally have altered PTEN expression (e.g. PTEN knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MARK gene that results in a decrease of MARK function, preferably such that MARK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MARK gene is used to construct a homologous recombination vector suitable for altering an endogenous MARK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MARK gene, e.g., by introduction of additional copies of MARK, or by operatively inserting a regulatory sequence that provides for altered expression of an endogenous copy of the MARK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the PTEN pathway, as animal models of disease and disorders implicating defective PTEN function, and for in vivo testing of candidate therapeutic agents, such as those identified in screens described below. The candidate therapeutic agents are administered to a genetically modified animal having altered MARK function and phenotypic changes are compared with appropriate control animals such as genetically modified animals that receive placebo treatment, and/or animals with unaltered MARK expression that receive candidate therapeutic agent.

In addition to the above-described genetically modified animals having altered MARK function, animal models having defective PTEN function (and otherwise normal MARK function), can be used in the methods of the present invention. For example, a mouse with defective DAF18 function can be used to assess, in vivo, the activity of a candidate DAF18 modulating agent identified in one of the its vitro assays described below. Transgenic mice with defective DAF18/PTEN function have been described in literature (DiCristofano A et al (1998) Nat genet 19:348-355). Preferably, the candidate PTEN modulating agent when administered to a model system with cells defective in PTEN function, produces a detectable phenotypic change in the model system indicating that the PTEN function is restored, i.e., the cells exhibit normal cell cycle progression.

Modulating Agents

The invention provides methods to identify agents that interact with and/or modulate the function of MARK and/or the PTEN pathway. Modulating agents identified by the methods are also part of the invention. Such agents are useful in a variety of diagnostic and therapeutic applications associated with the PTEN pathway, as well as in further analysis of the MARK protein and its contribution to the PTEN pathway. Accordingly, the invention also provides methods for modulating the PTEN pathway comprising the step of specifically modulating MARK activity by administering a MARK-interacting or modulating agent.

As used herein, an "MARK-modulating agent" is any agent that modulates MARK function, for example, an agent that interacts with MARK to inhibit or enhance MARK activity or otherwise affect normal MARK function. MARK function can be affected at any level, including transcription, protein expression, protein localization, and cellular or extracellular activity. In a preferred embodiment, the MARK-modulating agent specifically modulates the function of the MARK. The phrases "specific modulating agent", "specifically modulates", etc., are used herein to refer to modulating agents that directly bind to the MARK polypeptide or nucleic acid, and preferably inhibit, enhance, or otherwise alter, the function of the MARK. These phrases also encompass modulating agents that alter the interaction of the MARK with a binding partner, substrate, or cofactor (e.g. by binding to a binding partner of a MARK, or to a protein/binding partner complex, and altering MARK function). In a further preferred embodiment, the MARK-modulating agent is a modulator of the PTEN pathway (e.g. it restores and/or upregulates PTEN function) and thus is also a PTEN-modulating agent.

Preferred MARK-modulating agents include small molecule-compounds; MARK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the MARK protein or may be identified by screening compound libraries. Alternative appropriate modulators of this class are natural products, particularly secondary metabolites from organisms such as plants or fungi, which can also be identified by screening compound libraries for MARK-modulating activity. Methods for generating and obtaining compounds are well known in the art (Schreiber S L, Science (2000) 151: 1964-1969; Radmann J and Gunther J, Science (2000) 15-1947-1948).

Small molecule modulators identified from screening assays, as described below, can be used as lead compounds from which candidate clinical compounds may be designed, optimized, and synthesized. Such clinical compounds may have utility in treating pathologies associated with the PTEN pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MARK-interacting proteins are useful in a variety of diagnostic and therapeutic applications related to the PTEN pathway and related disorders, as well as in validation assays for other MARK-modulating agents. In a preferred embodiment, MARK-interacting proteins affect normal MARK function, including transcription, protein expression, protein localization, and cellular or extra-cellular activity. In another embodiment, MARK-interacting proteins are useful in detecting and providing information about the function of MARK proteins, as is relevant to PTEN related disorders, such as cancer (e.g., for diagnostic means).

An MARK-interacting protein may be endogenous, i.e. one that naturally interacts genetically or biochemically with a MARK, such as a member of the MARK pathway that modulates MARK expression, localization, and/or activity. MARK-modulators include dominant negative forms of MARK-interacting proteins and of MARK proteins themselves. Yeast two-hybrid and variant screens offer preferred methods for identifying endogenous MARK-interacting proteins (Finley, R. L. et al. (1996) in DNA Cloning-Expression Systems: A Practical Approach; eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928, 868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An MARK-interacting protein may be an exogenous protein, such as a MARK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MARK antibodies are further discussed below.

In preferred embodiments, a MARK-interacting protein specifically binds a MARK protein. In alternative preferred embodiments, a MARK-modulating agent binds a MARK substrate, binding partner, or cofactor.

Antibodies

In another embodiment, the protein modulator is a MARK specific antibody angonist or antagonist. The antibodies have therapeutic and diagnostic utilities, and can be used in screening assays to identify MARK modulators. The antibodies can also be used in dissecting the portions of the MARK pathway responsible for various cellular responses and in the general processing and maturation of the MARK.

Antibodies that specifically bind MARK polypeptides can be generated using known methods. Preferably the antibody is specific to a mammalian ortholog of MARK polypeptide, and more preferably, to human MARK. Antibodies may be polyclonal, monoclonal (mAbs), humanized or chimeric antibodies, single chain antibodies, Fab fragments, F(ab').sub.2 fragments, fragments produced by a FAb expression library, anti-idiotypic idiotypic (anti-Id) antibodies, and epitope-binding fragments of any of the above. Epitopes of MARK which are particularly antigenic can be selected, for example, by routine screening of MARK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219: 660-66) to the amino acid sequence of a MARK. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed)-Academic Press, New York; and U.S. Pat. Nos. 4,381,292; 4,451,570; and 4,618,577). Antibodies may be generated against crude cell extracts of MARK or substantially purified fragments thereof. If MARK fragments are used, they preferably comprise at least 10, and more preferably, at least 20 contiguous amino acids of a MARK protein. In a particular embodiment, MARK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MARK-specific antibodies is assayed by an appropriate assay such as a solid phase enzyme-linked immunosorbant assay (ELISA) using immobilized corresponding MARK polypeptides. Other assays, such as radioimmunoassays or fluorescent assays might also be used.

Chimeric antibodies specific to MARK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, While retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585, 089, 5,693,762, and 6,180,370).

MARK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or noncovalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg—to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Nucleic Acid Modulators

Other preferred MARK-modulating agents comprise nucleic acid molecules, such as antisense oligomers or double stranded RNA (dsRNA), which generally inhibit MARK activity. Preferred nucleic acid modulators interfere with the function of the MARK nucleic acid such as DNA replication, transcription, translocation of the MARK RNA to the site of protein translation, translation of protein from the MARK RNA, splicing of the MARK RNA to yield one or more mRNA species, or catalytic activity which may be engaged in or facilitated by the MARK RNA.

In one embodiment, the antisense oligomer is an oligonucleotide that is sufficiently complementary to a MARK mRNA to bind to and prevent translation, preferably by binding to the 5' untranslated region. MARK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide cat be modified at the base moiety, sugar moiety, or phosphate backbone. The oligonucleotide may include other appending groups such as peptides, agents that facilitate transport across the cell membrane, hybridization triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphordiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000).22(3):271-281; Summerton J, and Weller D. 1997 Antisense Nucleic Acid Drug Dev.:7:187-95; U.S. Pat. No. 5,235,033; and U.S. Pat. No. 5,378,841).

Alternative preferred MARK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36-1923-1937; Tonkinson J L et al., Antisense Oligodeoxynucleotides as Clinical Therapeutic Agents, Cancer Invest. (1996) 14:54-65). Accordingly, in one aspect of the invention, a MARK-specific nucleic acid modulator is used in an assay to further elucidate the role of the MARK in the PTEN pathway, and/or its relationship to other members of the pathway. In another aspect of the invention, a MARK-specific antisense oligomer is used as a therapeutic agent for treatment of PTEN-related disease states.

Assay Systems

The invention provides assay systems and screening methods for identifying specific modulators of MARK activity. As used herein, an "assay system" encompasses all the components required for performing and analyzing results of an assay that detects and/or measures a particular event. In general, primary assays are used to identify or confirm a modulator's specific biochemical or molecular effect with respect to the MARK nucleic acid or protein. In general, secondary assays further assess the activity of a MARK modulating agent identified by a primary assay and may confirm that the modulating agent affects MARK in a manner relevant to the PTEN pathway. In some cases, MARK modulators will be directly tested in a secondary assay.

In a preferred embodiment, the screening method comprises contacting a suitable assay system comprising a MARK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MARK activity, and hence the PTEN pathway. The MARK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric; spectrophotometric, and amperometric methods, to provide a read-out for the particular molecular event detected.

Cell-based screening assays usually require systems for recombinant expression of MARK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MARK-interacting proteins are used in screens to identify small molecule modulators, the binding specificity of the interacting protein to the MARK protein may be assayed by various known methods such as substrate processing (e.g. ability of the candidate MARK-specific binding agents to function as negative effectors in MARK-expressing cells), binding equilibrium constants (usually at least about $10^7 \text{ M}^{-1}$, preferably at least about $10^8 \text{ M}^{-1}$, more preferably at least about $10^9 \text{ M}^{-1}$), and immunogenicity (e.g. ability to elicit MARK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MARK polypeptide, a fusion protein thereof, or to cells or membranes bearing the polypeptide or fusion protein. The MARK polypeptide can be full length or a fragment thereof that retains functional MARK activity. The MARK polypeptide may be fused to another polypeptide, such as a peptide tag for detection or anchoring, or to another tag. The MARK polypeptide is preferably human MARK, or is an ortholog or derivative thereof as described above. In a preferred embodiment, the screening assay detects candidate agent-based modulation of MARK interaction with a binding target, such as an endogenous or exogenous protein or other substrate that has MARK—specific binding activity, and can be used to assess normal MARK gene function.

Suitable assay formats that may be adapted to screen for MARK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MARK and PTEN pathway modulators (e.g. U.S. Pat. No. 6,165,992 (kinase assays); U.S. Pat. Nos. 5,550,019 and 6,133,437 (apoptosis assays); and U.S. Pat. Nos. 5,976, 782, 6,225,118 and 6,444,434 (angiogenesis assays), among others). Specific preferred assays are described in more detail below.

Kinase Assays.

In some preferred embodiments the screening assay detects the ability of the test agent to modulate the kinase activity of a MARK polypeptide. In further embodiments, a cell-free kinase assay system is used to identify a candidate PTEN modulating agent, and a secondary, cell-based assay, such as an apoptosis or hypoxic induction assay (described below), may be used to further characterize the candidate PTEN modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem Jul. 1, 1996; 238(2): 159-64).

Apoptosis Assays.

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-317 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membranes breaks down, allowing for accumulation in the cytoplasm. Nucleosomes are not present in the cytoplasmic fraction of cells that are not undergoing apoptosis. An apoptosis assay system may comprise a cell that expresses a MARK, and that optionally has defective PTEN function (e.g. PTEN is over-expressed or under-expressed relative to wild-type cells). A test agent can be added to the apoptosis assay system and changes in induction of apoptosis relative to controls where no test agent is added, identify candidate PTEN modulating agents. In some embodiments of the invention, an apoptosis assay may be used as a secondary assay to test a candidate PTEN modulating agents that is initially identified using a cell-free assay system. An apoptosis assay may also be used to test whether MARK function plays a direct role in apoptosis. For example, an apoptosis assay may be performed on cells that over- or under-express MARK relative to wild type cells. Differences in apoptotic response compared to wild type cells suggests that the MARK plays a direct role in the apoptotic response. Apoptosis assays are described further in U.S. Pat. No. 6,133,437.

Cell Proliferation and Cell Cycle Assays.

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using $[^3H]$-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate $[^3H]$-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.# G5421).

Cell proliferation may also be assayed by colony formation in soft agar (Sambrook et al., Molecular Cloning, Cold Spring Harbor (1989)). For example, cells transformed with MARK are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a MARK may be stained with propidium iodide and evaluated in a flow cytometer (available from Becton Dickinson), which indicates accumulation of cells in different stages of the cell; cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses a MARK, and that optionally has defective PTEN function (e.g. PTEN is over-expressed or under-expressed relative to wild-type cells). A test agent can be added to the assay system and changes in cell proliferation or cell cycle relative to controls where no test agent is added, identify candidate PTEN modulating agents. In some embodiments of the invention, the cell proliferation or cell cycle assay may be used as a secondary assay to test a candidate PTEN modulating agents that is initially identified using another assay system such as a cell-free assay system. A cell proliferation assay may also be used to test whether MARK function plays a direct role in cell proliferation or cell cycle. For example, a cell proliferation or cell cycle assay may be performed on cells that over or under-express MARK relative to wild type cells. Differences in proliferation or cell cycle compared to wild type cells suggests that the MARK plays a direct role in cell proliferation or cell cycle.

Angiogenesis.

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a MARK, and that optionally has defective PTEN function (e.g. PTEN is over-expressed or underexpressed relative to wild-type cells). A test agent can be added to the angiogenesis assay system and changes in angiogenesis relative to controls where no test agent is added, identify candidate PTEN modulating agents. In some embodiments of the invention, the angiogenesis assay may be used as a secondary assay to test a candidate PTEN modulating agents that is initially identified using another assay system. An angiogenesis assay may also be used to test whether MARK function plays a direct role in cell proliferation. For example, an angiogenesis assay may be performed on cells that over- or under-express MARK relative to wild type cells. Differences in angiogenesis compared to wild type cells suggests that the MARK plays a direct role in angiogenesis. U.S. Pat. Nos. 5,976,782, 6,225,118 and 6,444,434, among others, describe various angiogenesis assays.

Hypoxic Induction.

The alpha subunit of the transcription factor, hypoxia inducible factor-1 (HIF-1), is upregulated in tumor cells following exposure to hypoxia in vitro. Under hypoxie conditions, HIF-1 stimulates the expression of genes known to be important in tumour cell survival, such as those encoding glycolytic enzymes and VEGF. Induction of such genes by hypoxic conditions may be assayed by growing cells transfected with MARK in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a MARK, and that optionally has defective PTEN function (e.g. PTEN is over-expressed or under-expressed relative to wild-type cells). A test agent can be added to the hypoxic induction assay system and changes in hypoxic response relative to controls where no test agent is added, identify candidate PTEN modulating agents. In some embodiments of the invention, the hypoxic induction assay may be used as a secondary assay to test a candidate PTEN modulating agents that is initially identified using another assay system. A hypoxic induction assay may also be used to test whether MARK function plays a direct role in the hypoxic response. For example, a hypoxic induction assay may be performed on cells that over- or under-express MARK relative to wild type cells. Differences in hypoxic response compared to wild type cells suggests that the MARK plays a direct role in hypoxic induction.

Cell Adhesion.

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice; In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. May-June 2001; 12(3):346-53).

Tubulogenesis.

Tubulogenesis assays monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpa. Thus, in a further preferred embodiment, a tubulogenesis assay system comprises testing a MARK's response to a variety of factors, such as FGF, VEGF, phorbol myristate acetate (PMA), TNF-alpha, ephrin, etc.

Cell Migration.

An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hematoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a MARK's response to a variety of pro-angiogenic factors, including tumor angiogenic and inflammatory angiogenic agents, and culturing the cells in serum free medium.

Sprouting Assay.

A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the MARK protein. Methods for testing antibody affinity and specificity are well known in the art (Harlow and Lane, 1988, 1999, supra). The enzyme-linked immunosorbant assay (ELISA) is a preferred method for detecting MARK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance MARK gene expression, preferably mRNA expression. In general, expression analysis comprises comparing MARK expression in like populations of cells (e.g., two pools of cells that endogenously or recombinantly express MARK) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that MARK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MARK protein or specific pep tides. A variety of means including Western blotting, ELISA, or in situ detection, are available (Harlow E and Lane D, 1988 and 1999, supra).

In some cases, screening assays described for small molecule modulators, particularly in assay systems that involve MARK mRNA expression, may also be used to test nucleic acid modulators.

Secondary Assays

Secondary assays may be used to further assess the activity of MARK-modulating agent identified by any of the above methods to confirm that the modulating agent affects MARK in a manner relevant to the PTEN pathway. As used herein, MARK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MARK.

Secondary assays generally compare like populations of cells or animals (e.g., two pools of cells or animals that endogenously or recombinantly express MARK) in the presence and absence of the candidate modulator. In general, such assays test whether treatment of cells or animals with a candidate MARK-modulating agent results in changes in the PTEN pathway in comparison to untreated (or mock- or placebo-treated) cells or animals. Certain assays use "sensitized genetic backgrounds", which, as used herein, describe cells or animals engineered for altered expression of genes in the PTEN or interacting pathways.

Cell-Based Assays

Cell based assays may detect endogenous PTEN pathway activity or may rely on recombinant expression of PTEN pathway components. Any of the aforementioned assays may be used in this cell-based format. Candidate modulators are typically added to the cell media but may also be injected into cells or delivered by any other efficacious means.

Animal Assays

A variety of non-human animal models of normal or defective PTEN pathway may be used to test candidate MARK modulators. Models for defective PTEN pathway typically use genetically modified animals that have been engineered to mis-express (e.g., over-express or lack expression in) genes involved in the PTEN pathway. Assays generally require systemic delivery of the candidate modulators, such as by oral administration, injection, etc.

In a preferred embodiment, PTEN pathway activity is assessed by monitoring neovascularization and angiogenesis. Animal models with defective and normal PTEN are used to test the candidate modulator's affect on MARK in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the MARK. The mixture is then injected subcutaneously(SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MARK is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the MARK endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorigenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorigenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science, 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific MARK-modulating agents are useful in a variety of diagnostic and therapeutic applications where disease or disease prognosis is related to defects in the PTEN pathway, such as angiogenic, apoptotic, or cell proliferation disorders. Accordingly, the invention also provides methods for modulating the PTEN pathway in a cell, preferably a cell pre-determined to have defective or impaired PTEN function (e.g. due to overexpression, underexpression, or misexpression of PTEN, or due to gene mutations), comprising the step of administering an agent to the cell that specifically modulates MARK activity. Preferably, the modulating agent produces a detectable phenotypic change in the cell indicating that the PTEN function is restored. The phrase "function is restored", and equivalents, as used herein, means that the desired phenotype is achieved, or is brought closer to normal compared to untreated cells. For example, with restored PTEN function, cell proliferation and/or progression through cell cycle may normalize, or be brought closer to normal relative to untreated cells. The invention also provides methods for treating disorders or disease associated with impaired PTEN function by administering a therapeutically effective amount of a MARK-modulating agent that modulates the PTEN pathway. The invention further provides methods for modulating MARK function in a cell, preferably a cell pre-determined to have defective or impaired MARK function, by administering a MARK-modulating agent. Additionally, the invention provides a method for treating disorders or disease associated with impaired ARK function by administering a therapeutically effective amount of a MARK-modulating agent.

The discovery that MARK is implicated in PTEN pathway provides for a variety of methods that can be employed for the diagnostic and prognostic evaluation of diseases and disorders involving defects in the PTEN pathway and for the identification of subjects having a predisposition to such diseases and disorders.

Various expression analysis methods can be used to diagnose whether MARK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective PTEN signaling that express a MARK, are identified as amenable to treatment with a MARK modulating agent. In a preferred application, the PTEN defective tissue overexpresses a MARK relative to normal tissue. For example, a Northern blot analysis of mRNA from tumor and normal cell lines, or from tumor and matching normal tissue samples from the same patient, using full or partial MARK cDNA sequences as probes, can determine whether particular tumors express or overexpress MARK. Alternatively, the Taq- Man® is used for quantitative RT-PCR analysis of MARK expression in cell lines, normal tissues and tumor samples (PE Applied Biosystems).

Various other diagnostic methods may be performed, for example, utilizing reagents such as the MARK oligonucleotides, and antibodies directed against a MARK, as described above for: (1) the detection of the presence of MARK gene mutations, or the detection of either over- or under-expression of MARK mRNA relative to the non-disorder state; (2) the detection of either an over- or an under-abundance of MARK gene product relative to the non-disorder state; and (3) the detection of perturbations or abnormalities in the signal transduction pathway mediated by MARK.

Kits for detecting expression of MARK in various samples, comprising at least one antibody specific to MARK, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in MARK expression, the method comprising: a) obtaining a biological sample from the patient; b) contacting the sample with a probe for MARK expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. C. elegans PTEN Screen

We designed a genetic screen to identify suppressor genes that, when inactivated, decrease signaling through the AKT pathway. The function of individual genes was inactivated by RNAi in the daf-18 (ep496); daf-2 (e1370) double mutant by soaking L1 larvae in double-stranded RNA for each gene. Subsequently, the larvae were grown on bacteria at 25° C. and scored for a statistically significant increase in dauer formation as compared to larvae treated without RNA (approximately 0-2% dauers). Suppressor genes were counter-screened to eliminate those that showed allele-specific suppression of the ep496 nonsense mutation but not the ep497 missense mutation by performing RNAi on the daf-18 (ep497); daf-2 (e1370) double mutant and scoring for enhanced dauer formation at 25° C. daf-16 mutations provide a test for pathway specificity since they fully suppress the Daf-c phenotype of all known AKT pathway mutants but, at most, only weakly suppress the Daf-c phenotype of mutants in the daf-7 (TGF-☐) and daf-11 (cGMP signaling) pathways. Therefore, we also counter-screened suppressor genes to eliminate those that increased dauer formation in a daf-18 (ep496); daf-1 (e1370); daf-16 (mgDf47) triple mutant. PAR-1 was an identified modifier. Orthologs of the modifiers are referred to herein as MARK.

BLAST analysis (Altschul et al., supra) was employed to identify orthologs of C. elegans modifiers. For example, representative sequences from MARK, GIs#27597094, 14133229, and 38569460 (SEQ ID NOs:15, 16, and 18, respectively) share 52%, 51%, and 54% amino acid identity, respectively, with the C. elegans PAR-1.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markdv model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the Caenorhabditis elegans genome and identification of human orthologs. Genome Res. November 2000; 10(11): 1679-89) programs. For example, the kinase domain (PFAM 00069) of MARK from GI#s 27597094, 14133229, and 38569460 (SEQ ID NOs:15, 16, and 18, respectively) is located respectively at approximately amino acid residues 27 to 278, 116 to 367, and 20 to 271.

II. High-Throughput In Vitro Fluorescence Polarization Assay

Fluorescently-labeled MARK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MARK activity.

III. High-Throughput In Vitro Binding Assay.

$^{33}$P-labeled MARK peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutrality-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate PTEN modulating agents.

IV. Immunoprecipitations and Immunoblotting

For coprecipitation of transfected proteins, $3 \times 10^6$ appropriate recombinant cells containing the MARK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 heat 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified MARK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, U C Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor—average (all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator; Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection-method.

TABLE 1

| | SEQ ID NO | |
|---|---|---|
| | 8 | 5 |
| Breast | 8% | 22% |
| # of Pairs | 36 | 36 |
| Colon | 5% | 21% |
| # of Pairs | 41 | 38 |
| Head And Neck | 0% | 23% |
| # of Pairs | 13 | 13 |
| Kidney | 5% | 10% |
| # of Pairs | 22 | 20 |
| Liver | 11% | 25% |
| # of Pairs | 9 | 8 |
| Lung | 0% | 13% |
| # of Pairs | 42 | 38 |
| Lymphoma | 0% | 0% |
| # of Pairs | 4 | 4 |
| Ovary | 0% | 16% |
| # of Pairs | 19 | 19 |
| Pancreas | 58% | 31% |
| # of Pairs | 12 | 13 |
| Prostate | 8% | 4% |
| # of Pairs | 24 | 24 |
| Skin | 14% | 14% |
| # of Pairs | 7 | 7 |
| Stomach | 0% | 0% |
| # of Pairs | 11 | 11 |
| Testis | 0% | 0% |
| # of Pairs | 8 | 8 |
| Thyroid Gland | 0% | 29% |
| # of Pairs | 14 | 14 |
| Uterus | 0% | 4% |
| # of Pairs | 23 | 23 |

VII. MARK Functional Assays

RNAi experiments were carried out to knock down expression of MARK sequences (SEQ ID NOs:5, 8, and 10) in various cell lines using small interfering RNAs (siRNA, Elbashir et al, supra).

Effect of MARK RNAi on cell proliferation and growth. BrdU and Cell Titer-Glo™ assays, described above, were employed to study the effects of decreased MARK expression on cell proliferation. The results of these experiments indicated that RNAi of SEQ ID NO:5 decreased proliferation in 231T breast cancer and HCT116 colon cancer cells; RNAi of SEQ ID NO:8 and SEQ ID NO: 10 decreased proliferation in 231T breast cancer, PC3 prostate cancer, and HCT116 colon cancer cells. MTS and [$^3$]-thymidine incorporation cell proliferation assays, as described above, were also employed to study the effects of decreased MARK expression on cell proliferation. The results of these experiment indicated that RNAi of SEQ ID NOs:5 and 8 decreased proliferation in PC3 prostate cancer cells, A549 lung cancer, and RD1 rhabdomyosarcoma cells in both assays. RNAi of SEQ ID NO:10 decreased proliferation in PC3 prostate cancer cells, A549 lung cancer, and RD1 rhabdomyosarcoma cells in the MTS assay, and PC3 prostate cancer cells and A549 lung cancer cells in the [$^3$H]-thymidine assay. Standard colony growth assays, as described above, were employed to study the effects of decreased MARK expression on cell growth. Decreased expression of SEQ ID NO:5 led to decreased cell growth in PC3 prostate cancer cells, SW480 colon cancer cells, and RD1 rhabdomyosarcoma cells; decreased expression of SEQ ID NOs:8 and 10 each led to decreased cell growth in A549 lung cancer cells, PC3 prostate cancer cells, SW480 colon cancer cells, and RD1 rhabdomyosarcoma cells.

Effect of MARK RNAi on apoptosis. Nucleosome ELISA apoptosis assay, as described above, was employed to study the effects of decreased MARK expression on apoptosis. Decreased expression of SEQ ID NO:5, 8, and 10 each led to apoptosis in A549 lung cancer cells.

MARK overexpression analysis. MARK (SEQ ID NO:5) was overexpressed in MDCK cells and tested in colony growth assays as described above. Overexpressed SEQ ID NO:5 had morphological effects on cells, and moderate effects on colony growth. Further, when transfected along with RAS in NIH3T3 cells, SEQ ID NO:5 caused transformation of the cells, as compared with vector alone, RAS alone, or SEQ ID NO:5 alone. Effects of overexpressed MARK on expression of various transcription factors was also studied. Overexpressed SEQ ID NO:5 caused an increased expression of the EGR (Early growth response) and SRE (Serum response element).

MARK FOXO nuclear translocation assays. FOXO nuclear translocation assays, as described above, were employed to assess involvement of MARK in the PTEN/IGF pathway. In these experiments, cells with reduced expression of MARK by RNAi were transiently transfected with a plasmid expressing GFP-tagged FOXO. Automated imaging of cellular components, such as nucleus and cytoplasm were then carried out to assess translocation of FOXO. Results indicated that reduced expression of SEQ ID NO:5, 8, and 10 each led to retention of FOXO in the nucleus, similar to a reduced AKT effect in PC3 prostate cancer cells. In another set of experiments, cells were co-transfected with siRNA directed to MARK along with a plasmid containing FOXO, and a cassette containing a promoter, a FOXO response element, and luciferase. Cells were then analyzed for luciferase activity and compared with cells with no siRNA. Results indicated that reduced expression of SEQ ID NO:5 led to retention of FOXO in the nucleus, similar to a reduced AKT effect. These results suggest involvement of MARK in the PTEN/IGF pathway.

---

What is claimed is:

1. A method of identifying a phosphatase and tensin homolog (PTEN) pathway modulating agent, said method comprising the steps of:
   (a) providing a first assay system comprising SEQ ID NO: 5 (a polynucleotide that encodes sucrose non-fermenting like kinase-1; SNF1LK) or a functionally active fragment thereof, wherein the functionally active fragment encodes a polypeptide comprising amino acid residues 27-278 of SNF1LK and has kinase activity, and wherein the assay system is capable of detecting the expression or activity of SEQ ID NO: 5;
   (b) contacting the first assay system with a test agent that modulates the expression or activity of SEQ ID NO: 5;
   (c) identifying the test agent as a PTEN pathway modulating agent by determining a difference in the expression or activity of SEQ ID NO: 5 in the assay system in the presence of the test agent of step (b) compared with the expression or activity of SEQ ID NO: 5 in the absence of the test agent;
   (d) providing a second assay system comprising cultured cells expressing SEQ ID NO: 5 that measures a change in the PTEN pathway, wherein the assay is a FOXO nuclear translocation assay;
   (e) contacting the second assay system with the test agent of step (b); and
   (f) confirming the test agent as a PTEN pathway modulating agent by determining a change in the PTEN pathway in the second assay system in the presence of said test agent compared with the absence of said test agent.

2. The method of claim 1, wherein the first assay system includes an expression assay comprising SEQ ID NO: 5 and the candidate test agent is a nucleic acid modulator that modulates the expression of SEQ ID NO: 5.

3. The method of claim 2, wherein the nucleic acid modulator is an antisense oligomer.

4. The method of claim 2, wherein the nucleic acid modulator is a phosphothioate morpholino oligomer (PMO).

5. The method of claim 2, wherein the nucleic acid modulator is a dsRNA or an siRNA.

* * * * *